United States Patent
Smith et al.

(10) Patent No.: US 11,447,638 B2
(45) Date of Patent: Sep. 20, 2022

(54) ACETALANTHRAQUINONE DERIVATIVES USEFUL FOR CELLULAR STAINING

(71) Applicant: BIOSTATUS LIMITED, Loughborough (GB)

(72) Inventors: Paul James Smith, Cowbridge South Glamorgan (GB); Rachel Jane Errington, Rhoose South Glamorgan (GB); Laurence Hylton Patterson, Skipton (GB); Klaus Pors, Shipley (GB); Laura Cosentino, Philadelphia, PA (US)

(73) Assignee: BIOSTATUS LIMITED, Loughborough (GB)

( * ) Notice: Subject to any disclaimer, the term of this patent is extended or adjusted under 35 U.S.C. 154(b) by 668 days.

(21) Appl. No.: 16/312,652

(22) PCT Filed: Jun. 9, 2017

(86) PCT No.: PCT/GB2017/051702
§ 371 (c)(1),
(2) Date: Dec. 21, 2018

(87) PCT Pub. No.: WO2017/220969
PCT Pub. Date: Dec. 28, 2017

(65) Prior Publication Data
US 2019/0249011 A1  Aug. 15, 2019

(30) Foreign Application Priority Data
Jun. 23, 2016  (GB) .................................... 1610971

(51) Int. Cl.
*C09B 1/26* (2006.01)
*C12Q 1/6841* (2018.01)
(Continued)

(52) U.S. Cl.
CPC ............ *C09B 1/262* (2013.01); *C07C 225/34* (2013.01); *C07C 225/36* (2013.01); *C09B 1/51* (2013.01);
(Continued)

(58) Field of Classification Search
CPC ...................................................... G01N 1/30
See application file for complete search history.

(56) References Cited

U.S. PATENT DOCUMENTS

| 4,597,905 A | 7/1986 | Edwards |
| 2010/0062460 A1 | 3/2010 | Pande et al. |
| 2010/0093004 A1 | 4/2010 | Patton et al. |

FOREIGN PATENT DOCUMENTS

| JP | S60172591 A | 9/1985 |
| JP | S61255897 A | 11/1986 |

(Continued)

OTHER PUBLICATIONS

The International Search Report and Written Opinion issued in PCT/GB2017/051702, dated Sep. 11, 2017. 20 pages.
(Continued)

*Primary Examiner* — Bin Shen
(74) *Attorney, Agent, or Firm* — Meunier Carlin & Curfman LLC

(57) ABSTRACT

The present invention provides di-substituted acetalanthraquinone-based compounds of the Formulae (I)-(IV) that are useful for cellular staining and for light-based detection of biological material, e.g. fluorescence-based detection of biological material. These compounds may be used in hydrolysed or non-hydrolysed form. Also provided is a fluorescent complex that comprises a nucleic acid and an acetalanthraquinone-based compound of the invention; and a method of staining a biological sample comprising cells or other biological material containing nucleic acid, which method comprises contacting the biological sample with an acetalanthraquinone-based compound of the invention. In the Formulae (I)-(IV), A and B are each independently of formula —$R^{a}CH_{2}CH(OR^{b})_{2}$; or one of A and B is of formula —$R^{a}CH_{2}CH(OR^{b})_{2}$ and the other one is of formula: —$NR^{b}{}_{2}$.

(Continued)

-continued

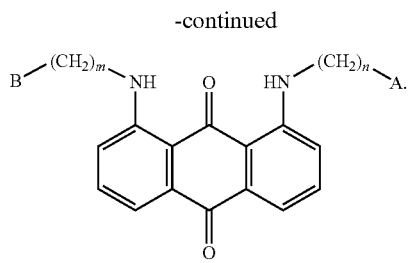

(IV)

27 Claims, 8 Drawing Sheets

(51) Int. Cl.
G01N 1/30 (2006.01)
G01N 33/50 (2006.01)
C09B 1/51 (2006.01)
C07C 225/36 (2006.01)
C07C 225/34 (2006.01)

(52) U.S. Cl.
CPC ............. *C12Q 1/6841* (2013.01); *G01N 1/30* (2013.01); *G01N 33/5008* (2013.01); *C07C 2603/24* (2017.05); *G01N 2001/302* (2013.01)

(56) References Cited

FOREIGN PATENT DOCUMENTS

| JP | H11100523 A | 4/1999 |
|---|---|---|
| WO | 199965992 A1 | 12/1999 |
| WO | 2010028349 A2 | 3/2010 |
| WO | 2010062499 A2 | 6/2010 |

OTHER PUBLICATIONS

XP009195340 (Wormser, H.C. et al. ): "A Facile Method for Preparing Substituted 1-Aminoanthraquinones" Synthetic Communications, vol. 23, No. 22, 1993, pp. 3211-3222.

Awasthi Pamita, et al. "Molecular modeling study of interaction of anthracenedione class of drug mitoxantrone and its analogs with DNA tetrameric sequences", Adv Exp Med Biol. 2011; 696: 385-400.

Gianoncelli, Alessandra, et al. Rational Design, Synthesis, and DNA Binding Properties of Novel Sequence-Selective Peptidyl Congeners of Ametantrone, ChemMedChem. Jul. 5, 2010;5(7):1080-91 (Abstract Only).

ACETALANTHRAQUINONE DERIVATIVES USEFUL FOR CELLULAR STAINING

FIELD OF THE INVENTION

The present invention relates to acetalanthraquinone-based compounds capable of cellular staining. The present invention also relates to the use of such compounds in the detection of biological materials, methods of analysing biological samples, and kits containing said compounds.

BACKGROUND TO THE INVENTION

Biological staining by fluorescent dyes is a principle used extensively in cytometric assays, including those designed to detect cells or subcellular components by flow cytometry and in vivo and in vitro imaging applications. Cell-based assays frequently exploit the capacity to differentiate cellular states through the use of fluorescent molecular probes which are either attached to affinity agents, such as antibodies, or through the intrinsic properties of a given compound enabling it to bind to cellular structures or to become differentially dispersed or accumulated throughout various cellular structures.

In image-based or flow-cytometry-based instrumentation and the like, the availability of sensitive detectors for differentiation or separation of fluorescence emissions and signatures is understood to be advantageous, due to the increasing use of multi-colour assays. Dyes that have preferential affinity for specific biological components are also desirable if binding does not compromise their efficient detection and prevent the quantification of a component of interest.

Fluorescent dyes with longer wavelength absorption and emission are particularly advantageous since they can be used in situations where biological materials have a background or inherent fluorescence or absorption in the visible range. Dyes that have differential abilities to distribute within biological structures, for example nuclear versus cytoplasmic compartments, can also provide multiple levels of cell identification and tracking.

An example of a cell-based assay is the Aldefluor assay (StemCell Technologies, as described in EP 1348124 B1). This is based on a reagent that is an acetal-derivative of a fluorescent molecule, which upon extracellular hydrolysis is able to enter an intact cell and undergo intracellular metabolism, thereby providing a determination of intracellular aldehyde dehydrogenase (ALDH) activity. The Aldefluor reagent, BODIPY-aminoacetaldehyde diethyl acetal (BAAA-DA), comprises a protected aldehyde moiety linked to the BODIPY fluor and is exposed to aqueous acid prior to cell treatment, converting it into BODIPY-amino-acetaldehyde (BAAA) capable of diffusion across the plasma membrane and subsequent metabolism by intracellular ALDH.

Anthraquinone (AQ) structures are also used in cell-based assays. AQ structures have near-IR fluorescence properties. They also have DNA affinity, although this is in varying degrees and is not necessarily readily predictable from their structures. The lack of fluorescence of specific AQ compounds has enabled the development of AQ compounds as quencher molecules that modify the fluorescent properties of other fluors when present in appropriate combinations. For example, WO/2004026804 A1 describes non-fluorescing anthraquinone compositions with strong fluorescence quenching properties.

Modification of AQ structures has yielded DNA-binding compounds that can enter live cells (as described in U.S. Pat. No. 6,468,753 B1 and in Smith, P. J., et al., Characteristics of a novel deep red/infrared fluorescent cell-permeant DNA probe, DRAQ5, in intact human cells analyzed by flow cytometry, confocal and multiphoton microscopy, Cytometry, 2000, 40(4), 280-91) or that are excluded from live cells but stain the nuclear material of dead or fixed cells (as described in US 20130101994 A1).

Real-time cell viability assays have also been described using the AQ derivative DRAQ7, a modified anthraquinone that is excluded from live cells but stains the nuclear material of dead or fixed cells (as described in Akagi, J., et al., Real-time cell viability assays using a new anthracycline derivative DRAQ7®. Cytometry Part A, 2013, 83 A(2), 227-234).

The cellular uptake and subcellular localisation of molecules can provide important information on the state of a cell or inform the pharmacokinetic properties of the molecule itself in a biological system of interest. The AQ anticancer drug mitoxantrone provides an example of how AQ molecules can offer advantageous properties for different detection modalities.

Mitoxantrone demonstrates a far-red fluorescence signature, permitting its uptake and subcellular distribution to be analysed by fluorescence microscopy and flow cytometry. This principle has been used to reveal drug resistant phenotypes of human tumour cells (as described in Smith P J et al., Subcellular distribution of the anticancer drug mitoxantrone in human and drug-resistant murine cells analyzed by flow cytometry and confocal microscopy and its relationship to the induction of DNA damage, Cancer Research 1992; 52:4000-8).

Alternative detection modalities can be employed beyond the property of intrinsic fluorescence. A property of molecules of interest in cell-based analyses and in diagnostic assays is that of Raman scattering. When a Raman active molecule, such as mitoxantrone, is irradiated with photons of a particular frequency Raman scattering occurs, whereby a minority of the incident photons interact with a vibrational mode of the irradiated molecule and are inelastically scattered. The inelastically scattered photons are shifted in frequency. The shift can be to a higher frequency (anti-Stokes) or to a lower frequency (Stokes). The Raman spectrum of frequency versus intensity provides a unique detection signal for the molecule.

Low signal-to-noise normally places a limitation on conventional Raman spectroscopy applications. The signal can, however, be increased by an intrinsic property of the molecule, such as high levels of cell permeation and accumulation. An alternative approach is to apply an enhancement methodology, as is known in the art, e.g.by surface-enhanced Raman scattering (SERS). In this regard, when a Raman-active molecule is adsorbed on or is in close proximity to a metal surface (e.g. gold or silver nanoparticles), the intensity of a Raman signal arising from the Raman-active molecule can be enhanced. The magnitude of the SERS-enhancement depends on a number of parameters, including the position and orientation of various bonds present in the Raman-active molecule with respect to the electromagnetic field at the metal surface. Bright signals, photostability, and narrow spectral features of SERS-active materials offer certain advantages for cell-based analyses, as described in Nolan J P et al, Surface-enhanced Raman scattering (SERS) cytometry, Methods in cell biology 2011; 102:515-32.

It is known that, in order to distinguish the species of interest from their cellular environment and other related molecules by Raman spectroscopy, compounds may be labelled with deuterium. This is described in Matthaus C et al, New ways of imaging uptake and intracellular fate of liposomal drug carrier systems inside individual cells, based on Raman microscopy, Molecular pharmaceutics 2008; 5:287-93.

It is also known that SERS spectroscopy can be used to reveal drug adsorption to the membrane environment of living cells. For example, SERS has been enabled by the addition of silver colloid to mitoxantrone-treated cells and provided a determination of the presence of the anticancer drug at the plasma membrane microenvironment of human tumour cells and its interaction with exogenously supplied nucleic acid. This is described in Breuzard, G. et al., Surface-enhanced Raman scattering reveals adsorption of mitoxantrone on plasma membrane of living cells, Biochem Biophys Res Commun., 2004, 320(2), pp. 615-621.

Molecules with intrinsic fluorescence and advantageous SERS properties can be analysed by combining modalities. For example, this is described in relation to the label-free bimodal imaging by confocal Raman and fluorescence spectroscopy of the intracellular drug release of mitoxantrone in Ganbold E O et al, Nonidentical intracellular drug release rates in Raman and fluorescence spectroscopic determination, Physical Chemistry Chemical Physics, 2015; 17:3019-23.

WO2008/154332 describes various near-infrared dyes and their use as surface-enhanced Raman scattering (SERS) reporter molecules. These are described as having enhanced SERS signals, allowing for their use in applications such as diagnostic assays using Raman spectroscopy as a detection method, optical imaging of tissues and cells, and other applications, where high sensitivity is required.

An alternative method of detection is one that exploits the "photoacoustic" effect. Absorption of laser light by chromophore(s) within a sample induces a thermoelastic expansion realized as an initial pressure rise, which then propagates as an acoustic wave. An ultrasonic transducer or transducer array detects the acoustic wave to form an image, which maps the original optical energy deposition in the tissue or cell sample. A given percentage change in the optical absorption coefficient yields the same percentage change in the photoacoustic amplitude with advantages for imaging in microscopy, cell evaluation and further biomedical applications.

A method for acquiring commonly used histological parameters from cultured cancer cells has been described in Moore, Michael J. et al, Evaluation of the morphological parameters of cancer cells using high-frequency ultrasound and photoacousties, 2015. Proceedings of the Ultrasonics Symposium (IMS), IEEE International, 10.1109/ULT-SYM.2015.0246, This details a hybrid ultra-high frequency acoustic/photoacoustic microscope used to determine cell nucleus-to-cytoplasm ratios by the analysis of backscattered ultrasound waves from cells stained with the DNA binding anthraquinone DRAQ5. In this case, the DNA binding properties of the dye specifically facilitated the generation of photoacoustic signals specifically from cell nuclei.

SUMMARY OF THE INVENTION

It has been recognised by the present inventors that there remains a demand for new molecular probes, in particular those with beneficial spectral characteristics in relation to different detection modalities, but also with advantageous cell and tissue penetration and/or subcellular distribution profiles. These would have use in cell detection, cell tracking, cell enumeration, and/or in the analysis of cellular integrity, state and function.

The present invention addresses the continuing need for molecular probes for fluorometric or other light-based detection analyses, and related assays employing different detection modalities. The compounds of the present invention have various beneficial properties that allow them to address deficiencies in the art.

The present invention provides acetalanthraquinone-based compounds that are useful for cellular staining and for light-based detection of biological material, e.g. fluorescence-based detection of biological material. These compounds may be used in hydrolysed or non-hydrolysed form.

According to a first aspect, the invention provides a compound of Formula (I):

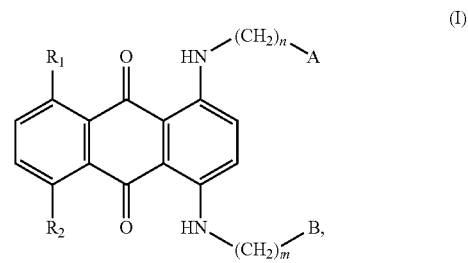

or hydrolysed forms thereof, or deuterated forms thereof, wherein
$R_1$ and $R_2$ are each independently selected from —OH or H, or $CH_3$, a halo group or OR, wherein R is selected from —$CH_3$, —$CH_2OCH_3$, —$CH(CH_3)_2$, —$COCH_3$, —$CH_2CHCH_2$, benzene and benzyl;
n and m are each independently an integer from 1 to 6, e.g. 1, 2, 3, 4 or 5;
and either:
(i) A and B are each independently of formula: —$R^aCH_2CH(OR^b)_2$;
or
(ii) one of A and B is of formula: —$R^aCH_2CH(OR^b)_2$ and the other one is of formula: —$NR^b_2$;
wherein
the or each $R^a$ is independently selected from —$CH_2$—, —C(=O)NH—, —NHC(=O)—, —C(=O)—, —C(=$CH_2$)—, —C(=$CH_2CH_3$)—, —N($CH_3$)—, and —N(alkylaryl)-
and the or each $R^b$ is independently selected from —$CH_3$, —$CH_2CH_3$, —$CH(CH_3)_2$, and —$CH_2CHCH_2$.

According to a second aspect, the invention provides a compound of Formula (II):

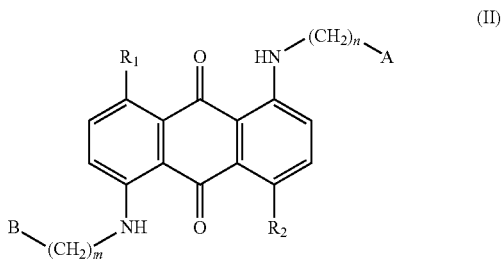

or hydrolysed forms thereof, or deuterated forms thereof, wherein
R₁ and R₂ are each independently selected from —OH or H, or CH₃, a halo group or OR, wherein R is selected from —CH₃, —CH₂OCH₃, —CH(CH₃)₂, —COCH₃, —CH₂CHCH₂, benzene and benzyl;
n and m are each independently an integer from 1 to 6, e.g. 1, 2, 3, 4 or 5;
and either:
(i) A and B are each independently of formula: —R$^a$CH₂CH(OR$^b$)₂;
or
(ii) one of A and B is of formula: —R$^a$CH₂CH(OR$^b$)₂ and the other one is of formula: —NR$^b$₂;
wherein
the or each R$^a$ is independently selected from —CH₂—, —C(=O)NH—, —NHC(=O)—, —C(=O)—, —C(=CH₂)—, —C(=CH₂CH₃)—, —N(CH₃)—, and —N(alkylaryl)-
and the or each R$^b$ is independently selected from —CH₃, —CH₂CH₃, —CH(CH₃)₂, and —CH₂CHCH₂.

According to a third aspect, the invention provides a compound of Formula (III):

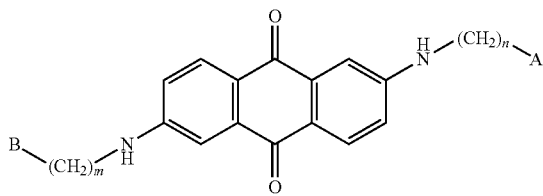

(III)

or hydrolysed forms thereof, or deuterated forms thereof, wherein
n and m are each independently an integer from 1 to 6, e.g. 1, 2, 3, 4 or 5;
and either:
(i) A and B are each independently of formula: —R$^a$CH₂CH(OR$^b$)₂;
or
(ii) one of A and B is of formula: —R$^a$CH₂CH(OR$^b$)₂ and the other one is of formula: —NR$^b$₂;
wherein
the or each R$^a$ is independently selected from —CH₂—, —C(=O)NH—, —NHC(=O)—, —C(=O)—, —C(=CH₂)—, —C(=CH₂CH₃)—, —N(CH₃)—, and —N(alkylaryl)-
and the or each R$^b$ is independently selected from —CH₃, —CH₂CH₃, —CH(CH₃)₂, and —CH₂CHCH₂.

According to a fourth aspect, the invention provides a compound of Formula (IV):

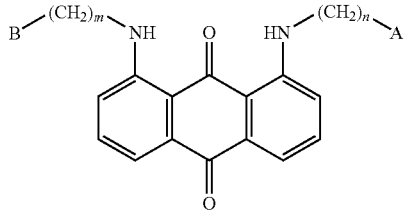

(IV)

or hydrolysed forms thereof, or deuterated forms thereof, wherein
n and m are each independently an integer from 1 to 6, e.g. 1, 2, 3, 4 or 5;
and either:
(i) A and B are each independently of formula: —R$^a$CH₂CH(OR$^b$)₂;
or
(ii) one of A and B is of formula: —R$^a$CH₂CH(OR$^b$)₂ and the other one is of formula: —NR$^b$₂;
wherein
the or each R$^a$ is independently selected from —CH₂—, —C(=O)NH—, —NHC(=O)—, —C(=O)—, —C(=CH₂)—, —C(=CH₂CH₃)—, —N(CH₃)—, and —N(alkylaryl)-
and the or each R$^b$ is independently selected from —CH₃, —CH₂CH₃, —CH(CH₃)₂, and —CH₂CHCH₂.

The present compounds have an affinity for nucleic acid molecules and can form a complex with nucleic acids, which can be detected optically.

The present compounds may be used in fluorescence-based technologies and assays or other light-based technologies and assays, e.g. based on Raman scattering or photoacoustic detection.

The compounds may be used to directly stain or label a sample so that the sample can be identified or quantified. For example, such compounds may be added as part of an assay for a biological target analyte or as a detectable tracer element in a biological or non-biological fluid.

The present compounds generally are utilized by combining the compound with a sample of interest under conditions selected to yield a detectable optical response.

The sample may be then illuminated at a wavelength selected to elicit the optical response.

In one embodiment the compounds are utilized by combining the compound with a sample of interest and then:
carrying out a fluorescence based detection step; or
carrying out a Raman scattering based detection step, e.g. a surface-enhanced Raman scattering (SERS) based detection step; or
carrying out a photoacoustic based detection step.

The present compounds have in particular been determined to have the following properties:

1. Near-IR fluorescence properties, permitting convenient signal detection and the variable expression of properties advantageous for the requirements of different forms of biological assays.

2. An intrinsic ability to bind to nucleic acids, thereby making them suitable for use in assays requiring nuclear discrimination.

3. Differential distribution within the cytoplasmic and nuclear compartments, thereby providing for pattern based recognition and image-masking methods using established analytical routines, including ratiometric approaches (typically nuclear to cytoplasmic ratio).

4. Cell permeation properties making them suitable for use in live cell applications, as well as suitable for use in fixed cell applications.

5. Low toxicity properties, making them suitable for use in protracted live cell assays (e.g. for the purpose of cell tracking).

Therefore the invention provides, in another aspect, the use of a compound of Formula (I) or Formula (II) or Formula (III) or Formula (IV) in light-based detection of biological materials, e.g. fluorescence-based detection of biological materials. It may be colorimetric, or photoacoustic, or Raman Scattering-based detection of biological materials.

In one embodiment, these biological materials comprise cellular and/or subcellular structures. In one embodiment, the biological materials comprise biological materials containing nucleic acid.

The invention provides in another aspect the use of a compound of Formula (I) or Formula (II) or Formula (III) or Formula (IV) in a biological assay, e.g. in an image-based assay.

The compound may provide one or more of the following functions in the assay: cell detection; cell tracking; cell enumeration; and determination of cellular integrity, state and function.

The invention provides in another aspect the use of a compound of Formula (I) or Formula (II) or Formula (III) or Formula (IV) as a nuclear and cytoplasmic differentiating counterstain.

According to a further aspect, the invention provides a fluorescent complex comprising a nucleic acid and a compound of Formula (I) or Formula (II) or Formula (III) or Formula (IV).

In one embodiment, the nucleic acid is DNA. In one embodiment, the DNA is present in a cell. In one embodiment, the DNA is present in a non-intact cell.

According to a yet further aspect, the invention provides a method of analysing a biological sample comprising cells, or other biological material containing nucleic acid, the method comprising the steps of:
a) preparing a biologically compatible solution containing a compound of Formula (I) or Formula (II) or Formula (III) or Formula (IV);
b) treating a biological sample with the biologically compatible solution; and
c) detecting a spectroscopic property associated with the absorption of electromagnetic radiation by the compound of Formula (I) or Formula (II) or Formula (III) or Formula (IV).

In such a method the spectroscopic property associated with absorption of electromagnetic radiation by the compound of Formula (I) or Formula (II) or Formula (III) or Formula (IV) may be fluorescence. Step c) may include exciting the compound with electromagnetic radiation, and detecting an emitted fluorescence signal.

In one embodiment, the spectroscopic property associated with absorption of electromagnetic radiation by the compounds of Formula (I) or Formula (II) or Formula (III) or Formula (IV) is a colorimetric property.

In one embodiment, the spectroscopic property associated with absorption of electromagnetic radiation by the compounds of Formula (I) or Formula (II) or Formula (III) or Formula (IV) is a photo acoustic property.

In one embodiment, the spectroscopic property associated with absorption of electromagnetic radiation by the compounds of Formula (I) or Formula (II) or Formula (III) or Formula (IV) is a Raman Scattering property.

In one embodiment, the method of analysing a biological sample further discriminates cellular nuclei in the cells, and step b) is performed to cause binding of nucleic acid in cellular nuclei by the compound of Formula (I) or Formula (II) or Formula (III) or Formula (IV), and the discrimination of the cellular nuclei is based at least in part on the spectroscopic property detected in step c).

In one embodiment, step b) is performed to stain the cells with the compound of Formula (I) or Formula (II) or Formula (III) or Formula (IV).

Cell death accruement may be monitored such that step b) is performed prior to or during an assay period thereby enabling a continuous or frequent readout of cell death accruement during the assay period.

Step c) may include detecting fluorescence emitted by individual cells by flow cytometry, or step c) may include intra-cellular location detection by fluorescence microscopy.

Therefore, detection of emitted fluorescence signals may be made with a variety of instruments including, but not limited to, microscopes, flow cytometers, plate readers and any variations thereof.

In one embodiment, the biological sample comprises cells, which may be fixed cells or permeabilised cells. The method therefore may analyse fixed or permeabilised cells, in which the cells are fixed by treatment with a fixative or permeabilising agent.

In one embodiment, step b) of the method further comprises treating the sample with at least one other fluorochrome or light-emitting compound, and step c) further comprises detecting a spectroscopic property associated with the absorption of electromagnetic radiation by the fluorochrome or light-emitting compound.

In yet another aspect, a method of staining a biological sample comprising cells or other biological material containing nucleic acid is provided, which method comprises contacting the biological sample with a compound of Formula (I) or Formula (II) or Formula (III) or Formula (IV).

It may be that the method comprises contacting the biological sample with the compound and then:
carrying out a fluorescence-based detection step; or
carrying out a Raman scattering-based detection step; or
carrying out a photoacoustic-based detection step.

In one embodiment, the method of staining a biological sample comprising cells or other biological material containing nucleic acid, comprises the steps of:
a) preparing a biologically compatible solution containing a compound of Formula (I) or Formula (II) or Formula (III) or Formula (IV);
b) treating a biological sample with the biologically compatible solution for a time sufficient to cause staining;
c) illuminating the stained sample with a light source sufficient to excite the compound of Formula (I) or Formula (II) or Formula (III) or Formula (IV); and
d) detecting the emitted fluorescence from the sample using a fluorescence detection instrument.

The sample may include a combination of the compound of Formula (I) or Formula (II) or Formula (III) or Formula (IV) and other fluorophores or dyes. For example, additional compound(s) may be present that emit in the UV or visible region of the spectrum upon excitation with an appropriate light source. The fluorescence spectra of the compounds described herein, by virtue of their relatively long emission wavelengths, make the compounds particularly useful in multiplex applications with fluorophores that emit in the UV or visible portion of the spectrum.

In one embodiment, the biological sample comprises fixed cells or permeabilized cells. In one embodiment, the biological sample comprises live cells, which may be in a form of a cell suspension or tissue sample.

Thus the methods as described herein may use live cells. Alternatively, the methods may use dead or fixed cells. It may be that the methods use a combination of cell types, e.g. selected from live and dead cells, fixed cells, permeabilized cells, and/or free cell nuclei. Cells may be treated with a cell fixative reagent, or a cell fixative reagent combined with a cell permeabilizing reagent, or a cell permeabilizing reagent.

The cells may be suspended in a fluid (e.g. a biological fluid or an aqueous fluid, such as buffer or water) or may be in a solid form, such as cells adhered to plates, coverslips, dishes, flasks, or the like or solid tissue samples that have been disaggregated.

For labelling of living cells, a compound of Formula (I) or Formula (II) or Formula (III) or Formula (IV), as described herein, is added to a sample containing living cells. The sample can include cells suspended in a buffer or media, or cells adhered to a glass or plastic surface, bathed in a buffer or media. For flow cytometry analysis, the compound can be added to the buffer or media containing living cells, incubated, and data acquired without washing the dye out of the sample. To ensure analysis is performed on living cells, a dead cell dye or a live cell dye may be included in the testing for gating out of dead cells or gating on living cells.

The present methods for detecting the presence of nucleic acids in a sample may further include quantification of the nucleic acid detected.

In yet another aspect, a method of quantifying nucleic acid content in live cells is provided, comprising: combining a compound of Formula (I) or Formula (II) or Formula (III) or Formula (IV), with a sample to form a mixture, wherein the sample comprises a nucleic acid molecule; incubating the mixture for a sufficient amount of time for the compound to associate with the nucleic acid in the sample; illuminating the incubated sample with an appropriate wavelength to generate a detectable optical response; and detecting the presence of nucleic acid in the sample by flow cytometric analysis, image cytometry analysis, image analysis including, or high content image analysis.

In yet another aspect, the present invention provides a kit for carrying out an assay, which includes a compound of Formula (I) or Formula (II) or Formula (III) or Formula (IV).

The compounds may be incorporated into kits that facilitate the practice of various assays. The kits may be packaged with the compound in a dry form or with the compound in solution. The kits may optionally further include one or more buffering agents, typically present as an aqueous solution, sample preparation reagents, additional detection reagents, organic solvent, other fluorescent detection probes, standards, microspheres, specific cell lines, antibodies and/or instructions for carrying out an assay. Additional optional agents include components for testing of other cell functions in conjunction with the compound.

DETAILED DESCRIPTION OF THE INVENTION

The present invention provides di-substituted acetalanthraquinone compounds. In one embodiment, these are 1,4-di-substituted (Formula (I)). In another embodiment, these are 1,5-di-substituted (Formula (II)). In a further embodiment, these are 2,6-di-substituted (Formula (III)). In a yet further embodiment, these are 1,8-di-substituted (Formula (IV)).

These compounds may optionally be provided in hydrolysed form. The skilled person would be readily able to hydrolyse the compounds as provided herein. This may be by acid-catalysed hydrolysis or base-catalysed hydrolysis. Such means of hydrolysis are well known, e.g. by refluxing in the presence of dilute hydrochloric acid or dilute sulphuric acid or sodium hydroxide solution. In one embodiment, the hydrolysis is acid-based, e.g. by exposure to 2M HCl for 30 minutes.

These compounds may optionally be provided in deuterated form. The skilled person would be readily able to deuterate the compounds as provided herein. This may be by applying the teachings of Matthaus C et al, New ways of imaging uptake and intracellular fate of liposomal drug carrier systems inside individual cells, based on Raman microscopy, Molecular pharmaceutics 2008; 5:287-93.

In the present invention, when the compound is chiral, it may be provided in the form of a single enantiomer or it may be provided in the form of a racemic mixture.

In general, in Formula (I) and Formula (II) $R_1$ and $R_2$ are each independently selected from —OH or H, or $CH_3$, a halo group (F, Cl, Br or I), or OR, wherein R is selected from —$CH_3$, —$CH_2OCH_3$, —$CH(CH_3)_2$, —$COCH_3$, —$CH_2CHCH_2$, benzene and benzyl. It may be that the halo group is F or Cl, e.g. Cl.

In one embodiment, the compounds are only di-substituted, i.e. in Formula (I) and Formula (II) $R_1$ and $R_2$ are both H.

In another embodiment, the compounds may include additional substitution, i.e. at least one of $R_1$ and $R_2$ is not H. In one embodiment both $R_1$ and $R_2$ are not H. For example, in Formula (I) and Formula (II) $R_1$ and $R_2$ may each independently selected from —OH, $CH_3$, and Cl. In one embodiment one or both of $R_1$ and $R_2$ is —OH.

In one preferred embodiment, $R_1$ and $R_2$ are the same. In one preferred embodiment, $R_1$ and $R_2$ are both —OH or are both H.

In the compounds of the invention n and m are each independently an integer from 1 to 6, e.g. 1, 2, 3, 4 or 5. It may be that n and m are each independently an integer from 1 to 3.

In one embodiment m and n are the same. In one embodiment m and n are both 1. In another embodiment m and n are both 2.

In one embodiment, option (i) applies and A and B are each independently of formula: —$R^aCH_2CH(OR^b)_2$; and m and n are the same. In one such embodiment m and n are 1 or 2 or 3 or 4 or 5. In one such embodiment m and n are 1 or 2. In one such embodiment m and n are 1.

In one embodiment, option (ii) applies and A is of formula: —$NR^b_2$ and B is of formula —$R^aCH_2CH(OR^b)_2$, m is 1 or 2 or 3 or 4 or 5 and n is 1 or 2 or 3. In one embodiment A is of formula: —$NR^b_2$ and B is of formula —$R^aCH_2CH(OR^b)_2$, m is 1 or 2 or 3 or 4 or 5 and n is 2.

In one embodiment, for option (i) or option (ii), the or each $R^a$ is independently selected from —$CH_2$—, —C(=O)NH—, —NHC(=O)—, —C(=O)—, —C(=CH_2)—, and —C(=CH_2CH_3)—. In one such embodiment the or each $R^a$ is independently selected from —$CH_2$—, —C(=O)NH—, —NHC(=O)—, —C(=O)—. In one such embodiment the or each $R^a$ is independently selected from —$CH_2$—, —C(=O)NH—, and —NHC(=O)—.

In one embodiment, for option (i) or option (ii), the or each $R^b$ is independently selected from —$CH_3$, —$CH_2CH_3$, and —$CH_2CHCH_2$. In one such embodiment the or each $R^b$ is independently selected from —$CH_3$, and —$CH_2CH_3$. In one embodiment the or each $R^b$ is —$CH_3$.

In one embodiment option (i) applies and A and B have the same $R^a$ group. In one such embodiment each $R^a$ is independently selected from —$CH_2$—, —C(=O)NH—, and —NHC(=O)—.

In one embodiment option (i) applies and A and B have the same $R^b$ group. In one such embodiment each $R^b$ is —$CH_3$.

In one embodiment option (i) applies A and B are the same.

In one embodiment option (ii) applies and A and B have the same $R^b$ group. In one such embodiment $R^b$ is —$CH_3$.

In one embodiment, the invention provides a compound of Formula (Ia):

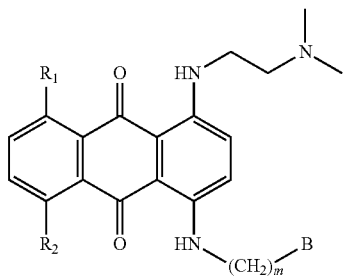

(Ia)

wherein
R$_1$ and R$_2$ are each independently selected from —OH or H,
B is —R$^a$CH$_2$CH(OCH$_3$)$_2$,
m is an integer selected from 1 to 6, e.g. 1 or 2 or 3 or 4 or 5;
and wherein R$^a$ is selected from —CH$_2$—, —C(=O)NH—, —NHC(=O)—, —C(=O)—, —C(=CH$_2$)—, —C(=CH$_2$CH$_3$)—, —N(CH$_3$)—, and —N(alkylaryl)-.

Preferably R$_1$ and R$_2$ are the same.

Preferably R$^a$ is selected from —CH$_2$—, —C(=O)NH—, —NHC(=O)—, —C(=O)—, —C(=CH$_2$)—, and —C(=CH$_2$CH$_3$)—. In one such embodiment R$^a$ is selected from —CH$_2$—, —C(=O)NH—, —NHC(=O)—, —C(=O)—. In one such embodiment R$^a$ is selected from —CH$_2$—, —C(=O)NH—, and —NHC(=O)—.

In one embodiment R$_1$ and R$_2$ are the same, m is 1 or 2, and R$^a$ is selected from —CH$_2$—, —C(=O)NH—, —NHC(=O)—, —C(=O)—, —C(=CH$_2$)—, and —C(=CH$_2$CH$_3$)—.

In one embodiment R$_1$ and R$_2$ are the same, m is 1 or 2, and R$^a$ is selected from —CH$_2$—, —C(=O)NH—, —NHC(=O)—, and —C(=O)—.

In one embodiment R$_1$ and R$_2$ are the same, m is 1 or 2, and R$^a$ is selected from —CH$_2$—, —C(=O)NH—, — and NHC(=O)—. In one such embodiment both R$_1$ and R$_2$ are H.

In one preferred embodiment, R$_1$ and R$_2$ are both H; m is 1; and R$^a$ is selected from —CH$_2$—, —C(=O)NH—, and —NHC(=O)—.

In another preferred embodiment, R$_1$ and R$_2$ are both —OH; m is 1; and R$^a$ is selected from —CH$_2$—, —C(=O)NH—, and —NHC(=O)—.

In one embodiment, the compound of Formula (Ia) is of the following formula:

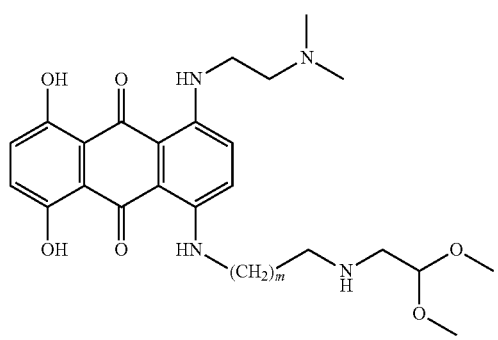

(Ib)

wherein m is an integer selected from 1, 2, 3, 4 and 5, e.g. it may be 1 or 2.

In one embodiment, the compound of Formula (I) is of the following formula:

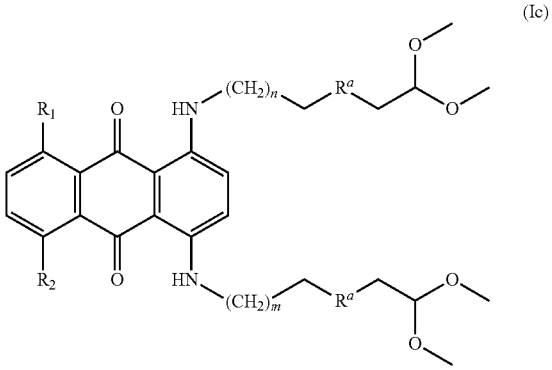

(Ic)

wherein
R$_1$ and R$_2$ are each independently selected from —OH or H,
m is an integer selected from 1 to 6.
and R$^a$ is selected from —CH$_2$—, —C(=O)NH—, —NHC(=O)—, —C(=O)—, —C(=CH$_2$)—, —C(=CH$_2$CH$_3$)—, —N(CH$_3$)—, and —N(alkylaryl)-.

Preferably R$_1$ and R$_2$ are the same.

Preferably R$^a$ is selected from —CH$_2$—, —C(=O)NH—, —NHC(=O)—, —C(=O)—, —C(=CH$_2$)—, and —C(=CH$_2$CH$_3$)—. In one such embodiment R$^a$ is selected from —CH$_2$—, —C(=O)NH—, —NHC(=O)—, —C(=O)—. In one such embodiment R$^a$ is selected from —CH$_2$—, —C(=O)NH—, and —NHC(=O)—.

In one embodiment R$_1$ and R$_2$ are the same, m is 1 or 2, and R$^a$ is selected from —CH$_2$—, —C(=O)NH—, —NHC(=O)—, —C(=O)—, —C(=CH$_2$)—, and —C(=CH$_2$CH$_3$)—.

In one embodiment R$_1$ and R$_2$ are the same, m is 1 or 2, and R$^a$ is selected from —CH$_2$—, —C(=O)NH—, —NHC(=O)—, and —C(=O)—.

In one embodiment R$_1$ and R$_2$ are the same, m is 1 or 2, and R$^a$ is selected from —CH$_2$—, —C(=O)NH—, — and NHC(=O)—. In one such embodiment both R$_1$ and R$_2$ are H.

In one preferred embodiment, R$_1$ and R$_2$ are both H; m is 1; and R$^a$ is selected from —CH$_2$—, —C(=O)NH—, and —NHC(=O)—.

In another preferred embodiment, R$_1$ and R$_2$ are both —OH; m is 1; and R$^a$ is selected from —CH$_2$—, —C(=O)NH—, and —NHC(=O)—.

In one preferred embodiment, R$_1$ and R$_2$ are H, m is 1; and R$^a$ is selected from —CH$_2$—, —C(=O)NH—, and —NHC(=O)—. Preferably, R$^a$ is —CH$_2$—.

In one embodiment, the compound of Formula (Ic) is of the following formula:

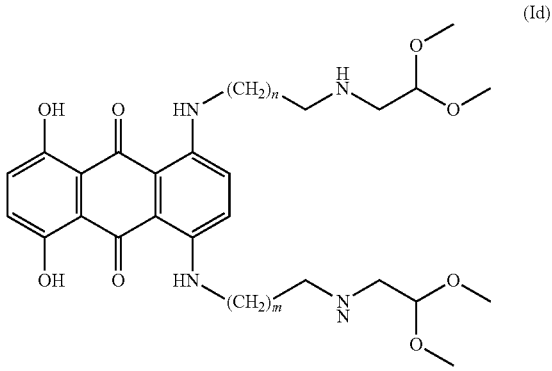

(Id)

wherein n and m are the same and are an integer selected from 1 to 6.

In one preferred embodiment, n and m are the same and are an integer selected from 1, 2, 3, 4 and 5. It may be that n and m are the same and are an integer selected from 1, 2, and 3. In one embodiment both n and m are 1.

The compounds of the present invention may have hydrolysable groups. The compounds may optionally be provided as a hydrolysed form or in use they may be hydrolysed. The hydrolysis of compounds is known in the art and the skilled person would be able to hydrolyse the compounds using known techniques. Acid-catalysed hydrolysis and base-catalysed hydrolysis are well known, e.g. refluxing in the presence of dilute hydrochloric acid or dilute sulphuric acid or sodium hydroxide solution.

The compounds of the invention can contain asymmetric carbon atoms and can therefore exist in racemic and optically active forms. Thus optical isomers or enantiomers, racemates, tautomers, and diastereomers are envisaged as being able to be used in the present invention.

In this regard, the methods of present invention include the use of all such isomers and mixtures thereof. Methods of separation of enantiomeric and diastereomeric mixtures are well known to one skilled in the art. For example, racemic forms can be resolved by physical methods, such as, e.g., fractional crystallization, separation or crystallization of diastereomeric derivatives or separation by chiral column chromatography. The individual optical isomers can be obtained from the racemates using conventional methods, such as, e.g., salt formation with an optically active acid followed by crystallization. The present invention encompasses any isolated racemic or optically active form of compounds of the invention, or any mixture thereof.

As used herein, the term "aryl" refers to a carbocyclic aromatic system containing one ring, or two or three rings fused together where in the ring atoms are all carbon. The term "aryl" includes, but is not limited to, groups such as phenyl, naphthyl, or anthracenyl.

As used herein, the term "alkyl" refers to a straight-chain or branched-chain alkyl group containing from 1 to 12 carbon atoms. A C1-z alkyl is an alkyl from 1 to z carbon atoms; thus, a C1-8 alkyl has from 1 to 8 carbon atoms, a C1-4 alkyl has from 1 to 4 carbon atoms and a C1-2 alkyl has from 1 to 2 carbon atoms. Examples of alkyl groups include, but are not limited to, methyl, ethyl, n-propyl, isopropyl, n-butyl, isobutyl, sec-butyl, tert-butyl, pentyl, isopentyl, neo-pentyl, iso-amyl, hexyl, heptyl, octyl, or nonyl.

As used herein, and unless otherwise stated, the term "alkylaryl" refers to a straight-chain or branched-chain alkyl group containing from 1 to 12 carbon atoms, e.g. from 1 to 10 carbon atoms, onto which an aryl group (such as defined above) is attached. Specific examples of the alkylaryl groups are those having 7 to 30 carbon atoms in total and in particular those wherein the alkyl group is a C1-6 straightchain or branched alkyl. For example, the alkylaryl group may be benzyl, phenylethyl, phenylpropyl, phenylbutyl, phenylpentyl or phenylhexyl.

Representative methods for preparing the acetalanthraquinone compounds of the invention are described in the Examples provided herein.

Embodiments of the present invention will now be described, by way of example only, with reference to the accompanying drawings, in which:

FIG. 1A shows absorption (line) and fluorescence (dots) spectra of compounds BST-108, BST-109, BST-110 and BST-111. The fluorescence spectra was obtained at excitation wavelengths of 610 nm; 584 nm; 583 nm; 610 nm respectively, representing peak excitation wavelengths.

FIG. 1B shows absorption (line) and fluorescence (dots) spectra of compounds BST-101, BST-100. BST-102 and BST-106. The fluorescence spectra was obtained at excitation wavelengths of 540 nm; 584 nm; 585 nm; 584 nm respectively, representing peak excitation wavelengths.

EXAMPLES

Figure 1A:
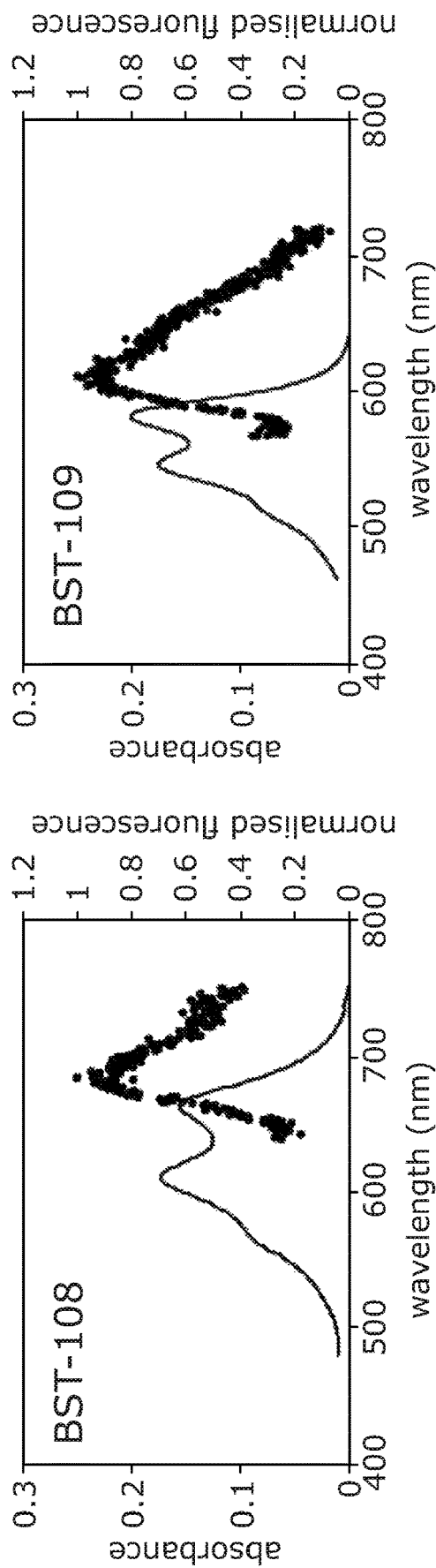
Figure 1A:
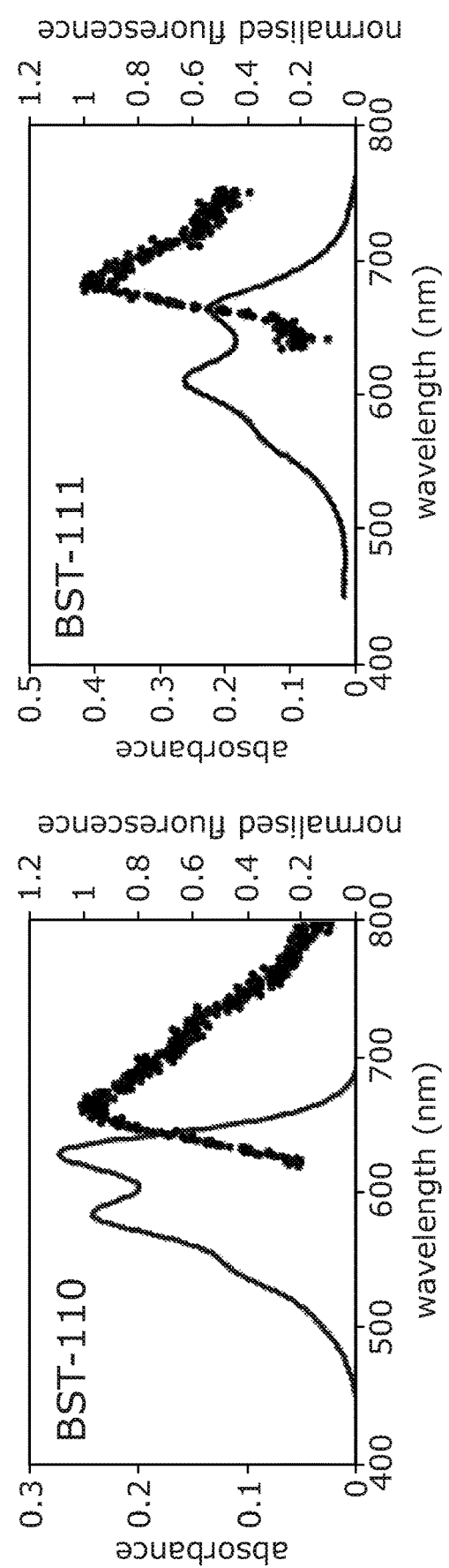

Production of the Compounds of the Invention

Compounds of Formula (I)-(IV) can be synthesized in accordance with, or in analogy to, the general routes described in the below Schemes:

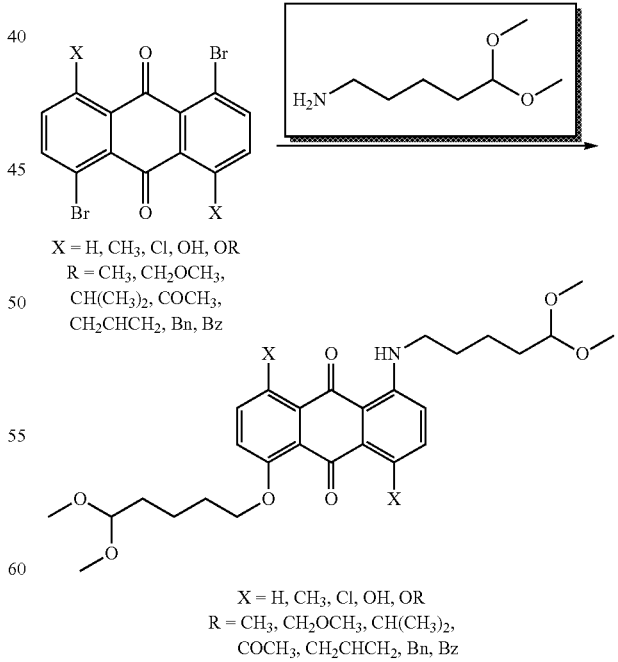

X = H, CH₃, Cl, OH, OR
R = CH₃, CH₂OCH₃,
CH(CH₃)₂, COCH₃,
CH₂CHCH₂, Bn, Bz

X = H, CH₃, Cl, OH, OR
R = CH₃, CH₂OCH₃, CH(CH₃)₂,
COCH₃, CH₂CHCH₂, Bn, Bz 1,5-disubstituted anthraquinone

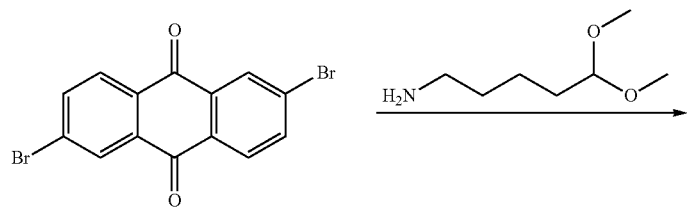

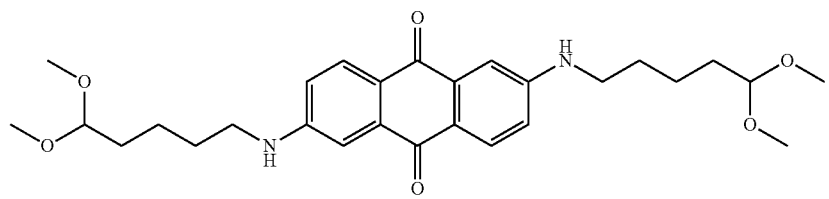

2,6-disubstituted anthraquinone

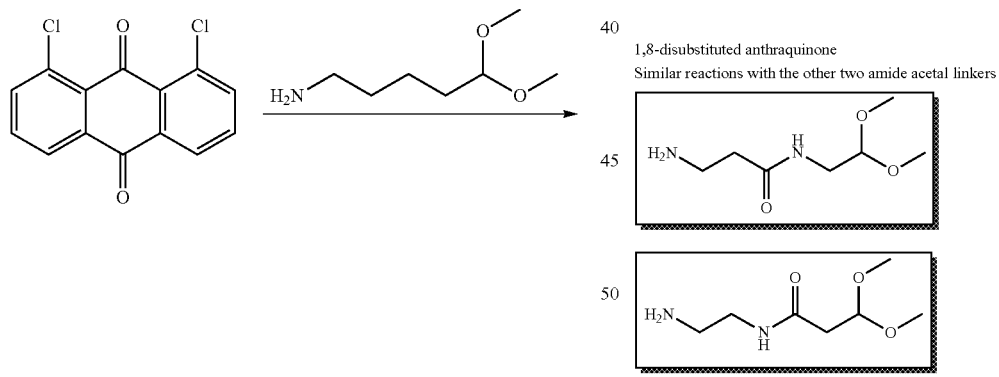

1,8-disubstituted anthraquinone
Similar reactions with the other two amide acetal linkers

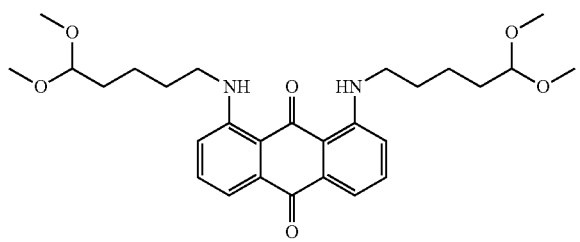

The compounds of Formula (I)-(IV) can be obtained by following the processes described below. Unless otherwise stated, in the methods described below the meanings of the substituent groups are the meanings described above with regard to a compound of Formula (I)-(IV).

The following compounds according to the invention were prepared and tested in the examples:—

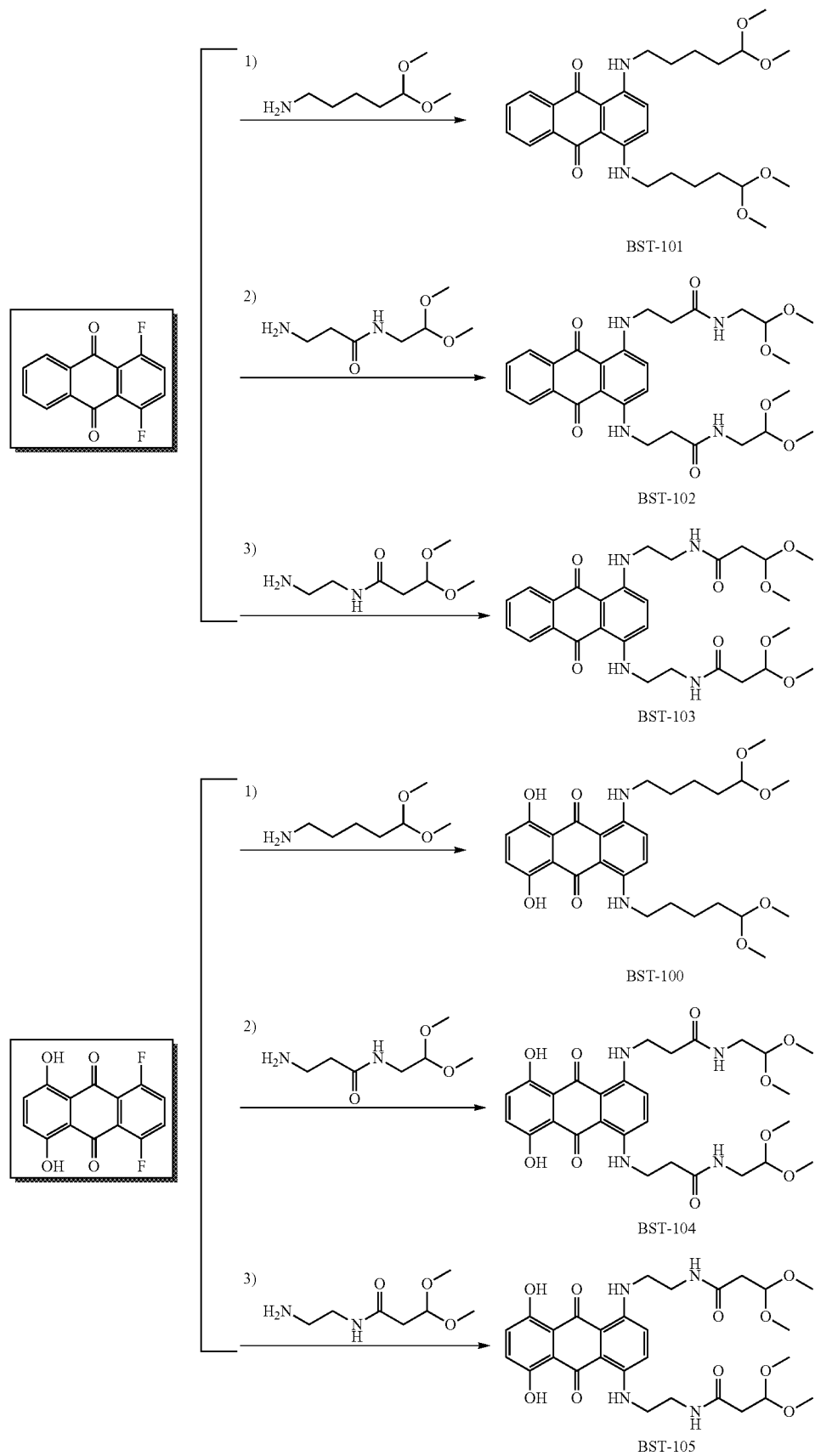

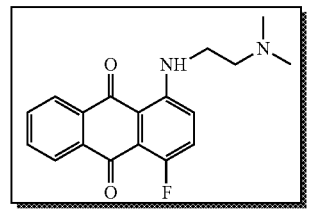
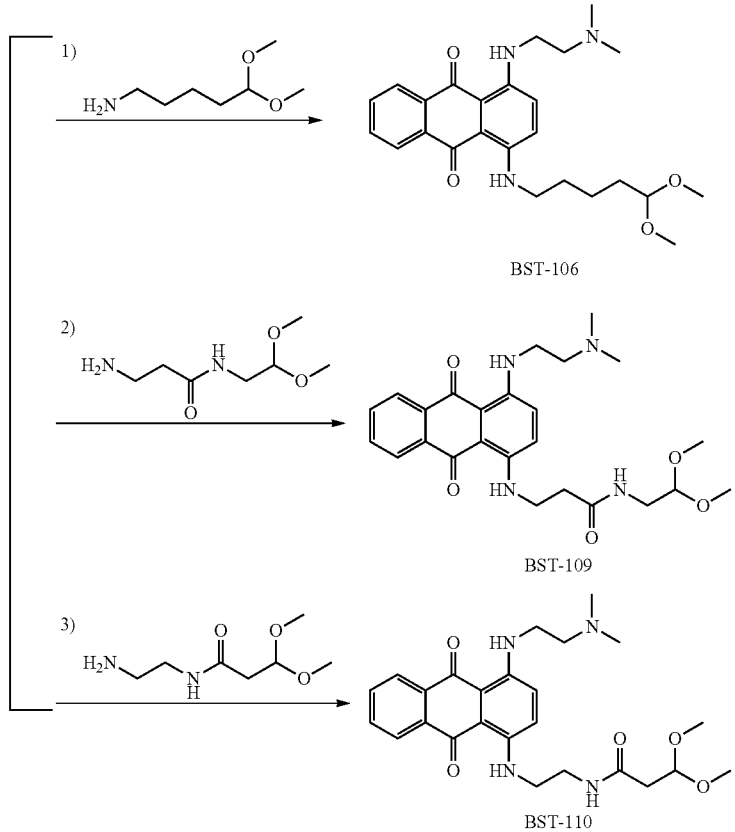
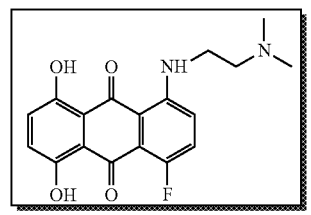
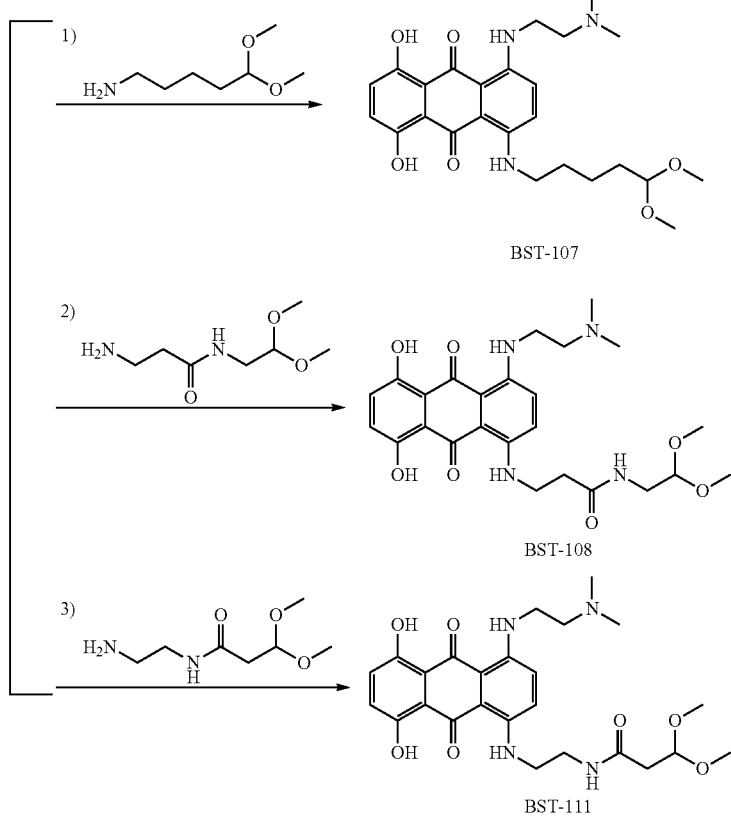

Example 1—Synthesis of Symmetrical
1,4-Di-Substituted-Anthraquinones (Formula (I))

The following specific compounds were synthesized:

Example 1a 1,4-Bis(5,5-dimethoxypentylamino)anthracene-9,10-dione (BST-101)

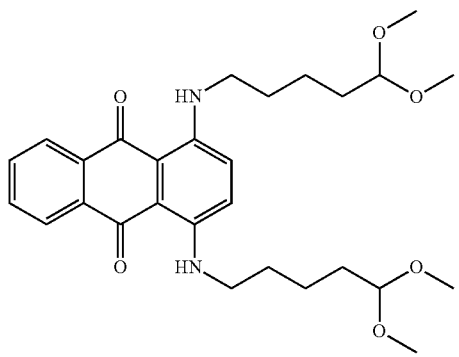 [SMILES: COC(CCCCNc1ccc(NCCCCC(OC)OC)c2c1C(=O)c1ccccc1C2=O)OC]

To a stirred solution of 1,4-difluoro-anthraquinone (74 mg, 0.29 mmol) in pyridine (1 mL) was added 5,5-dimethoxypentanamine (261 mg, 1.72 mmol) and the resulting solution was stirred at 70° C. for 3 h. The solvent was evaporated under reduced pressure and the reaction mixture was purified by flash chromatography using gradient eluent (EtOAc:PE, 0:100→3:7) to yield the title compound as a dark blue powder (62 mg, 44%). $\delta_H$ (CDCl$_3$, 400 MHz) 8.24 (2H, dd, J 3.5, 6.0 Hz), 7.6 (2H, dd, J 3.5, 6.0 Hz), 7.14 (2H, s), 4.32 (2H, t, J 5.6), 3.62 (4H, t, J 6.5 Hz), 3.36 (4H, t, J 5.5 Hz), 3.25 (12H, s, O(CH$_3$)$_2$), 1.75-1.45 (12H, m); $\delta_C$ (CDCl$_3$, 100 MHz) 181.3, 145, 133.5, 130.7, 125.3, 122.1, 108.7, 103.4, 51.7, 41.2, 30.8, 28.5, 21.1; m/z (ES+) 499 (M+H, 100).

Example 1b 3,3'-(9,10-Dioxo-9,10-dihydroanthracene-1,4-diyl)bis(azanediyl)bis(N-(2,2-dimethoxyethyl)propanamide) (BST-102)

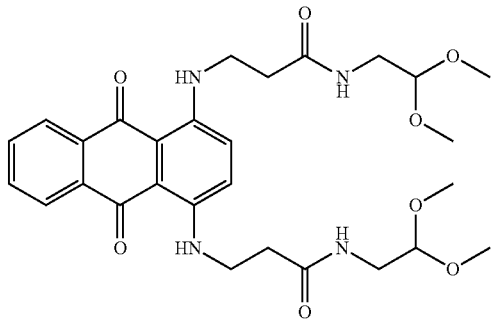 [SMILES: COC(CNC(=O)CCNc1ccc(NCCC(=O)NCC(OC)OC)c2c1C(=O)c1ccccc1C2=O)OC]

To a stirred solution of 1,4-difluoro-anthraquinone (80 mg, 0.33 mmol) in pyridine (1 mL) was added 3-amino-N-(2,2-dimethoxyethyl)propanamide (345.7 mg, 1.96 mmol) and the resulting solution was stirred at 70° C. for 4 h. The solvent was evaporated under reduced pressure and the reaction mixture was purified by flash chromatography using gradient eluent (CH$_3$OH:CH$_2$Cl$_2$, 1:99→4:9 to yield the title compound as a dark blue powder (107 mg, 59%). $\delta_H$ (CDCl$_3$, 400 MHz) 8.15 (2H, dd J 3.5, 6.0 Hz), 7.6 (2H, dd J 3.5, 6.0 Hz), 7.12 (2H, s), 4.32 (2H, t, J 5.6 Hz), 3.61 (4H, t, J 6.5 Hz), 3.37 (4H, t, J 5.6 Hz), 3.28 (12H, s, O(CH$_3$)$_2$), 2.53 (4H, t, J 6.5 Hz); $\delta_C$ (CDCl$_3$, 100 MHz) 182.2, 170.8, 145.6, 134.2, 132.1, 126.0, 123.3, 110.3, 102.8, 54.2, 41.2, 36.5, 39.1; m/z (ES+) 557 (M+H, 100).

Example 1c

N,N'-(2,2'-(9,10-Dioxo-9,10-dihydroanthracene-1,4-diyl)bis(azanediyl)bis(ethane-2,1-diyl))bis(3,3-dimethoxypropanamide) (BST-103)

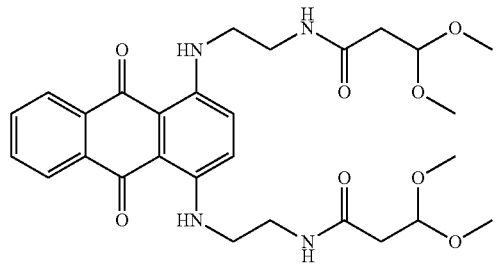 [SMILES: COC(CC(=O)NCCNc1ccc(NCCNC(=O)CC(OC)OC)c2c1C(=O)c1ccccc1C2=O)OC]

To a stirred solution of 1,4-difluoro-anthraquinone (80 mg, 0.33 mmol) in pyridine (1 mL) was added N-(2-aminoethyl)-3,3-dimethoxypropanamide (346 mg, 1.96 mmol) and the resulting solution was stirred at 70° C. for 4 h. The solvent was evaporated under reduced pressure and the reaction mixture was purified by flash chromatography using gradient eluent (CH$_3$OH:CH$_2$Cl$_2$, 1:99→4:9). After the chromatographic purification residual acidic aliphatic impurities were removed by washing with 0.1 M NaOH (2×10 mL), and brine (1×10 mL) before being dried over MgSO$_4$. After filtration, the solvent was concentrated in vacuo to yield the title compound as a dark blue powder (25 mg, 29%). $\delta_H$ (CDCl$_3$, 400 MHz) 8.10 (2H, dd, J 3.5, 6.0 Hz), 7.57 (2H, dd, J 3.0, 5.5 Hz), 7.06 (1H, br s, NH), 6.98 (2H, s), 5.20 (2H, s), 4.69 (2H, t, J 5.6 Hz), 3.51 (4H, t, J 6.0 Hz), 3.25 (12H, s, O(CH$_3$)$_2$), 2.60 (4H, d, J 5.6 Hz); $\delta_C$ (CDCl$_3$, 100 MHz) 182.2, 169.9, 168.3, 134.2, 132.1, 126.0, 123.2, 109.9, 102.3, 54.3, 42.1, 40.9, 39.2; m/z (ES+) 557 (M+H, 100).

Example 2—Synthesis of Non-Symmetrical 1,4-Di-Substituted-Anthraquinones (Formula (I))

The following specific compounds were synthesized:

Example 2a 1-(5,5-Dimethoxypentylamino)-4-(2-(dimethylamino)ethylamino) anthracene-9,10-dione (BST-106)

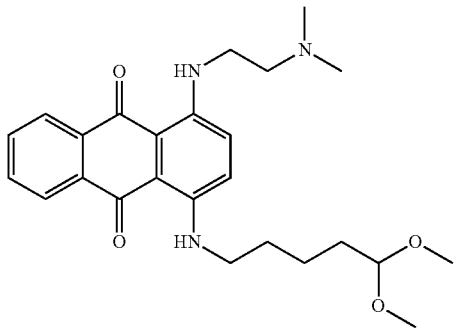 [SMILES: COC(CCCCNc1ccc(NCCN(C)C)c2c1C(=O)c1ccccc1C2=O)OC]

To a stirred solution of 1-(2-(dimethylamino)ethylamino)-4-fluoroanthracene-9,10-dione (60 mg, 0.19 mmol) in pyridine (1 mL) was added 5,5-dimethoxypentan-1-amine (113 mg, 0.77 mmol) and the resulting solution was stirred at 70° C. for 4 h. The solvent was evaporated under reduced pressure and the reaction mixture was purified by flash chromatography using gradient eluent ($CH_3OH:CH_2Cl_2$, 1:99→4:9) to yield the title compound as a dark blue powder (59 mg, 70%). $\delta_H$ ($CDCl_3$, 400 MHz) 10.7 (2H, br s, NH), 8.3 (2H, dd, J 4.0, 5.5 Hz), 7.6 (2H, dd, J 4.0, 5.5 Hz), 7.3 (2H, dd, J 6.0, 15.6 Hz), 4.32 (1H, t, J 5.6 Hz), 3.53 (2H, t, J 5.6 Hz), 3.33 (2H, t, J 6.5 Hz), 3.26 (6H, s), 2.72 (2H, t, J 6.5 Hz), 2.33 (6H, s), 1.7 (2H, m), 1.63 (2H, m), 1.42 (2H, m); $\delta_C$ ($CDCl_3$, 100 MHz) 182.7, 182.4, 146.6, 145.6, 134.5, 134.4, 132.1, 132.0, 126.2, 126.0, 123.6, 123.5, 110.2, 109.8, 104.4, 58.4, 52.9, 45.4, 45.39, 42.8, 40.7, 32.3, 29.5, 22.3; m/z (ES+) 440 (M+H, 100).

Example 2b

N-(2,2-Dimethoxyethyl)-3-(4-(2-(dimethylamino)ethylamino)-9,10-dioxo-9,10-dihydroanthracen-1-ylamino)propanamide (BST-109)

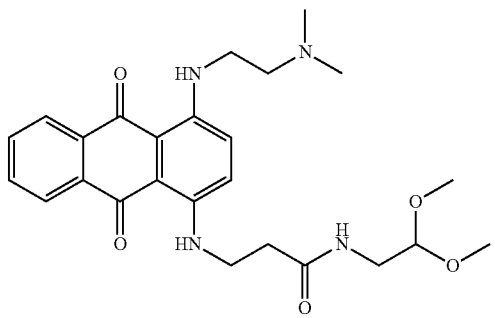 [SMILES: COC(CNC(=O)CCNc1ccc(NCCN(C)C)c2c1C(=O)c1ccccc1C2=O)OC]

To a stirred solution of 1-(2-(dimethylamino)ethylamino)-4-fluoroanthracene-9,10-dione (60 mg, 0.19 mmol) in pyridine (1 mL) was added 3-amino-N-(2,2-dimethoxyethyl)propanamide (135 mg, 0.77 mmol) and the resulting solution was stirred at 70° C. for 6 h. The solvent was evaporated under reduced pressure and the reaction mixture was purified by flash chromatography using gradient eluent ($CH_3OH:CH_2Cl_2$, 1:99→6:94) to yield the title compound as a dark blue powder (56 mg, 70%). $\delta_H$ ($CDCl_3$, 400 MHz) 10.6 (2H, br s, NH), 8.2 (2H, d, J 6.0 Hz), 7.5 (2H, d, J 5.5 Hz), 5.95 (1H, br s, NH), 4.37 (1H, t, J 5.3 Hz), 3.71, (2H, t, J 5.5 Hz), 3.5 (2H, t, J 5.5 Hz), 3.3 (2H, t, J 6.5 Hz), 3.25 (6H, s), 2.76 (2H, t, J 6.5 Hz), 2.54 (2H, t, J 5.5 Hz), 2.41 (6H, s); $\delta_C$ ($CDCl_3$, 100 MHz) 181.7, 181.7, 169.7, 144.7, 144.5, 133.3, 131.1, 125.1, 124.9, 122.5, 122.3, 109.2, 109.2, 101.5, 57.0, 53.4, 44.1, 40.0, 39.2, 38.1, 35.8; m/z (ES+) 469 (M+H, 100).

Example 2c

N-(2-(4-(2-(dimethylamino)ethylamino)-9,10-dioxo-9,10-dihydroanthracen-1-ylamino)ethyl)-3,3-dimethoxypropanamide (BST-110)

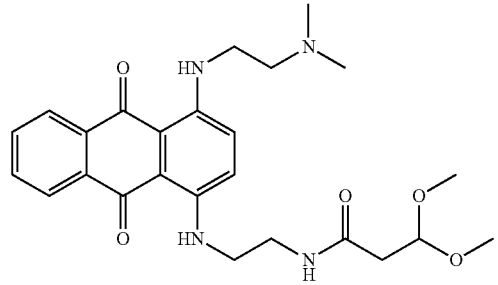 [SMILES: COC(CC(=O)NCCNc1ccc(NCCN(C)C)c2c1C(=O)c1ccccc1C2=O)OC]

To a stirred solution of 1-(2-(dimethylamino)ethylamino)-4-fluoroanthracene-9,10-dione (50 mg, 0.16 mmol) in pyridine (1 mL) was added N-(2-aminoethyl)-3,3-dimethoxypropanamide (112 mg, 0.64 mmol) and the resulting solution was heated under reflux for 4 h. The solvent was evaporated under reduced pressure and the reaction mixture was purified by flash chromatography using gradient eluent ($CH_3OH:CH_2Cl_2$, 1:99→6:94) to yield the title compound as a dark blue powder (45 mg, 60%). $\delta_H$ ($CDCl_3$, 400 MHz); 10.7 (1H, br s, NH), 10.6 (1H, br s, NH), 8.2 (2H, dq, J 4.5, 9.0 Hz), 7.64 (2H, dd, J 2.0, 4.0 Hz), 7.2 (2H, dd, J 9.6, 25.2 Hz), 6.71 (1H, NH br s), 4.6 (1H, t, J 5.5 Hz), 3.5 (2H, t, J 5.5 Hz), 3.2 (6H, s), 2.73 (2H, t, J 6.5 Hz), 2.59 (2H, t, J 6.5 Hz), 2.43 (2H, t, J 5.5 Hz), 2.37 (6H, s); $\delta_C$ ($CDCl_3$, 100 MHz) 182.7, 182.4, 169.8, 169.2, 169.1, 146.0, 145.9, 134.4, 134.3, 132.2, 126.0, 125.9, 123.4, 110.0, 102.3, 102.2, 101.9, 58.3, 54.1, 51.4, 45.4, 41.9, 40.7, 39.4, 37.0; m/z (ES+) 469 (M+H, 100).

Example 3—Synthesis of Symmetrical 1,4-di-substituted-5,8-dihydroxy-anthraquinones (Formula (I))

The following specific compounds were synthesized:

Example 3a 1,4-Bis(5,5-dimethoxypentylamino)-5,8-dihydroxy-anthracene-9,10-dione (BST-100)

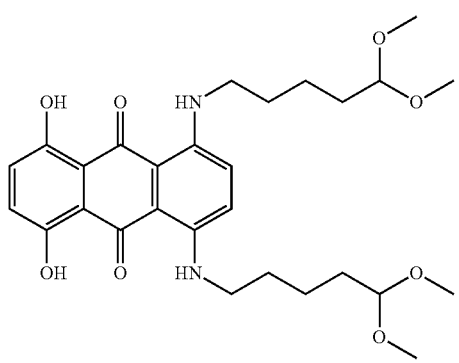 [SMILES: COC(CCCCNc1ccc(NCCCCC(OC)OC)c2c1C(=O)c1c(O)ccc(O)c1C2=O)OC]

To a stirred solution of 1,4-difluoro-5,8-dihydroxyanthracene-9,10-dione (47 mg, 0.17 mmol) in pyridine (1 mL) was added 5,5-dimethoxypentan-1-amine (200 mg, 1.36 mmol) and the resulting solution was heated under reflux for 3 h. The reaction mixture was diluted with $CH_2Cl_2$ (20 mL) and washed with cold brine (2×10 mL). The organic solution was dried with $MgSO_4$, filtered and the remaining solution was concentrated in vacuo. The crude solid was purified by flash chromatography using gradient eluent (EtOAc:PE, 1:9→4:1) to yield the title compound as a dark blue powder (47 mg, 52%). $\delta_H$ (CDCl$_3$, 400 MHz) 13.14 (2H, s), 10.28 (2H, br s), 6.99 (2H, s), 6.96 (2H, s), 4.33 (2H, t, J 5.6 Hz), 3.27 (12H, s, O(CH$_3$)$_2$), 1.73-1.44 (8H, m), 1.19 (4H, s); $\delta_C$ (CDCl$_3$, 100 MHz) 183.8, 154.3, 145.4, 123.5, 122.7, 114.4, 107.6, 103.3, 51.8, 41.8, 28.3, 21.67, 13.1; m/z (ES+) 531 (M+H, 100).

Example 3b 3,3'-(5,8-dihydroxy-9,10-dioxo-9,10-dihydroanthracene-1,4diyl)bis(azanediyl)bis(N-(2,2-dimethoxyethyl)propanamide) (BST-104)

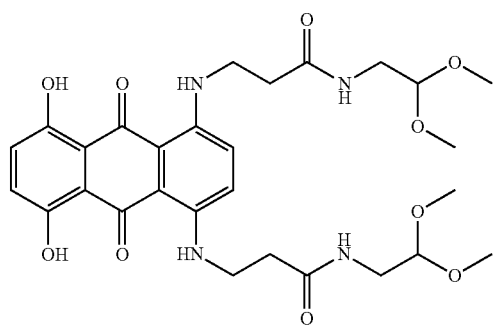 [SMILES: COC(CNC(=O)CCNc1ccc(NCCC(=O)NCC(OC)OC)c2c1C(=O)c1c(O)ccc(O)c1C2=O)OC]

To a stirred solution of 1,4-difluoro-5,8-dihydroxyanthracene-9,10-dione (80 mg, 0.29 mmol) in pyridine (1 mL) was added 3-amino-N-(2,2-dimethoxyethyl) propanamide (306. mg, 1.74 mmol) and the resulting solution was heated under reflux for 3 h. The solvent was evaporated under reduced pressure and the reaction mixture was purified by flash chromatography using gradient eluent (CH$_3$OH:CH$_2$Cl$_2$, 1:99→1:9) to yield the title compound as a dark blue powder (112 mg, 66%). $\delta_H$ (DMSO, 400 MHz) 13.4 (2H, s, OH), 10.6 (2H, br s, NH), 8.15 (2H, br s, NH), 7.47 (2H, s), 7.11 (2H, s), 4.32 (2H, t, J 5.55 Hz), 3.73 (4H, q, J 5.5 Hz), 3.30 (12H, s, O(CH$_3$)$_2$), 3.25 (4H, t, J 5.5 Hz), 2.43 (4H, m); $\delta_C$ (DMSO, 100 MHz) 183.3, 170.2, 154.5, 146.8, 125.4, 124.3, 114.9, 107.2, 102.1, 53.2, 40.5, 38.9, 35.2; m/z (ES+) 589 (M+H, 100).

Example 3c

N,N'-(2,2'-(5,8-Dihydroxy-9,10-dioxo-9,10-dihydroanthracene-1,4-diyl)bis(azanediyl)bis(ethane-2,1-diyl))bis(3,3-dimethoxypropanamide) (BST-105)

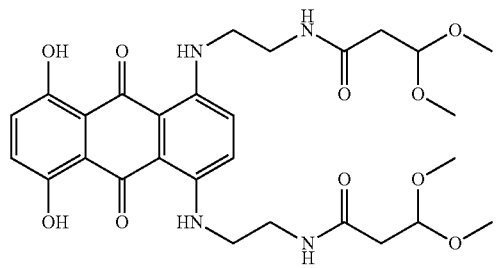 [SMILES: COC(CC(=O)NCCNc1ccc(NCCNC(=O)CC(OC)OC)c2c1C(=O)c1c(O)ccc(O)c1C2=O)OC]

To a stirred solution of 1,4-difluoro-5,8-dihydroxyanthracene-9,10-dione (71 mg, 0.26 mmol) in pyridine (1 mL) was added N-(2-aminoethyl)-3,3-dimethoxypropanamide (272 mg, 1.54 mmol) and the resulting solution was heated under reflux for 4 h. The solvent was evaporated under reduced pressure and the reaction mixture was purified by flash chromatography using gradient eluent (CH$_3$OH:CH$_2$Cl$_2$, 1:99→1:9) to yield the title compound as a dark blue powder (10 mg, 37%). $\delta_H$ (DMSO, 400 MHz) 13.5 (2H, s, OH), 10.7 (2H, br s, NH), 8.13 (2H, br s, NH), 7.64 (2H, s), 7.21 (2H, s), 4.72 (2H, t, J 5.5 Hz) 3.53 (4H, q, J 5.5 Hz), 3.35 (4H, t, J 5.5 Hz), 3.25 (12H, s, O(CH$_3$)$_2$); $\delta_C$ (DMSO, 100 MHz) 182.3, 172.2, 154.5, 140.9, 124.4, 124.3, 115.9, 108.5, 103.1, 53.7, 44.5, 38.9, 34.2; m/z (ES+) 589 (M+H, 100).

Example 3d 1,4-bis((2-((2,2-dimethoxyethyl)amino)ethyl)amino)-5,8-dihydroxyanthracene-9,10-dione (BST-200)

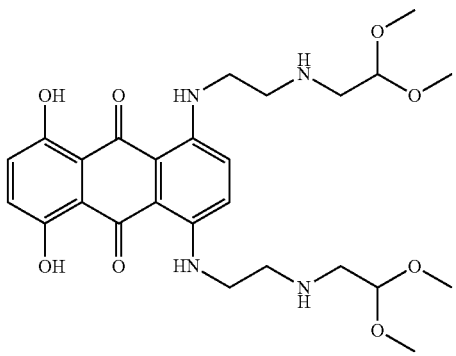 [SMILES: COC(CNCCNc1ccc(NCCNCC(OC)OC)c2c1C(=O)c1c(O)ccc(O)c1C2=O)OC]

To a stirred solution of 1,4-difluoro-5,8-dihydroxyanthracene-9,10-dione (50 mg, 0.18 mmol) in pyridine (1 mL) was added N-(2,2-dimethoxyethyl)ethane-1,2-diamine (205 mg, 1.38 mmol) and the resulting solution was heated under reflux for 4 h. The solvent was evaporated under reduced pressure and the reaction mixture was purified by flash chromatography using gradient eluent ($CH_3OH:CH_2Cl_2$, 1:99→4:9) to yield the title compound as a dark blue powder (45 mg, 47%). $\delta_H$ (CDCl$_3$, 400 MHz) 13.37 (2H, s br), 10.32 (2H, t, J 5H), 7.00 (2H, s), 6.97 (2H, s), 4.43 (2H, t, J 5.6 Hz), 3.39 (4H, q, J 5.6 Hz), 3.34 (12H, s), 2.93 (4H, t, J 6 Hz), 2.76 (4H, d, J 5.6 Hz); $\delta_C$ (CDCl$_3$, 101 MHz) 185.23, 155.41, 146.41, 124.71, 123.68, 115.35, 109.12, 103.94, 54.17, 51.03, 48.77, 43.01; m/z (ES+) 533 (M+H, 100). Anal. calculated for $C_{26}H_{36}N_4O_8$: C, 58.63; H, 6.81; N, 10.52. Found: C, 57.23; H, 6.46; N, 10.21.

Example 3e 1,4-bis((6-((2,2-dimethoxyethyl)amino)hexyl) amino)-5,8-dihydroxyanthracene-9,10-dione) (BST-300)

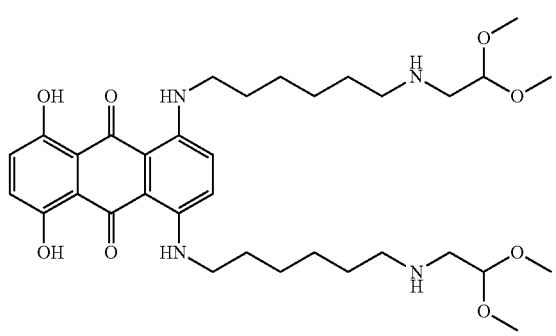 [SMILES: COC(CNCCCCCCNc1ccc(NCCCCCCNCC(OC)OC)c2c1C(=O)c1c(O)ccc(O)c1C2=O)OC]

To a stirred solution of 1,4-difluoro-5,8-dihydroxyanthracene-9,10-dione (33 mg, 0.12 mmol) in pyridine (1 mL) was added N-(2,2-dimethoxyethyl)hexane-1,6-diamine (200 mg, 0.99 mmol) and the resulting solution was stirred at 70° C. for 2 h. The solvent was evaporated under reduced pressure and the reaction mixture was purified by flash chromatography using gradient eluent ($CH_3OH:CH_2Cl_2$, 1:99→4:9 to yield the title compound as a dark blue powder (45 mg, 58%). $\delta_H$ (CDCl$_3$, 400 MHz) 13.45 (2H, s), 10.35 (2H, t, J 5H), 7.09 (2H, s), 7.04 (2H, s), 4.42 (2H, t, J 5.6 Hz), 3.32 (18H, s), 2.67 (4H, d, J 5.6 Hz), 2.58 (4H, m), 1.68 (4H, m), 1.45 (6H, m), 1.37 (6H, m); $\delta_C$ (CDCl$_3$, 101 MHz) 185.18, 155.44, 146.62, 124.70, 123.88, 115.48, 108.85, 103.81, 54.05, 51.18, 49.86, 42.98, 29.89, 29.51, 27.02, 27.00; m/z (ES+) 545 (M+H, 100). Anal. calculated for $C_{34}H_{52}N_4O_8$: C, 63.33; H, 8.13; N, 8.69. Found: C, 63.05; H, 7.98; N, 8.48.

Example 3f 1,4-bis((2-((2,2-dimethoxyethyl)(methyl)amino) ethyl)amino)-5,8-dihydroxyanthracene-9,10-dione (BST-201)

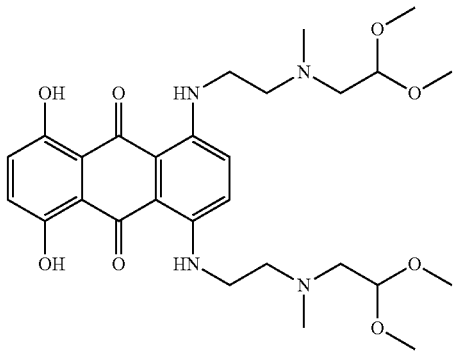 [SMILES: COC(CN(C)CCNc1ccc(NCCN(C)CC(OC)OC)c2c1C(=O)c1c(O)ccc(O)c1C2=O)OC]

To a stirred solution of 1,4-bis((2-((2,2-dimethoxyethyl) amino)ethyl)amino)-5,8-dihydroxyanthracene-9,10-dione (134 mg, 0.25 mmol) in DMF (3 mL) was added DIPEA (131 μL, 0.75 mmol) and methyl iodide (47 μL, 0.75 mmol) before the resulting solution was stirred at room temperature overnight. The solution was washed with saturated NaHCO$_3$ (2×10 mL) and the organic layer was dried with MgSO$_4$. The solvent was evaporated under reduced pressure and the reaction mixture was purified by flash chromatography using gradient eluent ($CH_3OH:CH_2Cl_2$, 1:99→6:94) to yield the title compound as a dark blue powder (63 mg, 45%). $\delta_H$ (CDCl$_3$, 400 MHz) 13.61 (2H, s, OH), 10.47 (2H, t, NH, J=5.5. Hz), 7.24 (2H, s), 7.14 (2H, s), 4.59 (2H, t, J 5.5 Hz) 3.51 (4H, q, J 5.5 Hz), 3.43 (12H, s, O(CH$_3$)$_2$), 2.85 (4H, t, J 5.5 Hz), 2.67 (4H, d, J 5.5 Hz), 2.44 (6H, s); $\delta_C$ (CDCl$_3$, 100 MHz) 185.58, 155.51, 146.32, 124.89, 124.02, 115.42, 109.31, 103.53, 59.54, 56.93, 53.84, 43.11, 41.04; m/z (ES+) 561 (M+H, 100).

Example 3g 1,4-bis((2-(benzyl(2,2-dimethoxyethyl)amino)ethyl) amino)-5,8-dihydroxyanthracene-9,10-dione (BST-202)

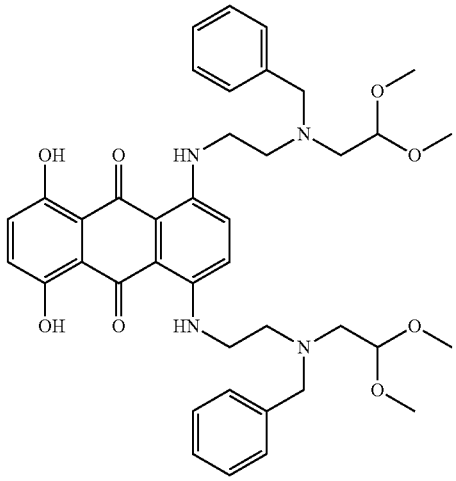 [SMILES: COC(CN(CCNc1ccc(NCCN(Cc2ccccc2)CC(OC)OC)c2c1C(=O)c1c(O)ccc(O)c1C2=O)Cc1ccccc1)OC]

To a stirred solution of 1,4-bis((2-((2,2-dimethoxyethyl) amino)ethyl)amino)-5,8-dihydroxyanthracene-9,10-dione (134 mg, 0.25 mmol) in CH$_2$Cl$_2$ (10 mL) was added DIPEA (174 µL) and benzyl bromide (118 µL) before the resulting solution was stirred at room temperature overnight. The solution was washed with saturated NaHCO₃ (2×10 mL) and the organic layer was dried with MgSO₄. The solvent was evaporated under reduced pressure and the reaction mixture was purified by flash chromatography using gradient eluent (CH₃OH:CH₂Cl₂, 1:99→6:94) to yield the title compound as a dark blue powder (124 mg, 93%). $\delta_H$ (CDCl₃, 400 MHz) 13.65 (2H, s, OH), 10.46 (2H, t, NH), 7.37 (4H, d, J 7.2 Hz), 7.17 (6H, m), 7.09 (2H, s), 6.99 (2H, s), 4.40 (2H, t, J 5.5 Hz), 3.69 (4H, s), 3.38 (4H, q, J 6 Hz), 3.25 (12H, s, O(CH₃)₂), 2.84 (4H, t, J 6 Hz), 2.49 (4H, d, J 5 Hz); $\delta_C$ (CDCl₃, 100 MHz) 185.4, 155.5, 146.3, 139.1, 128.9, 128.3, 127.2, 124.8, 124.1, 115.5, 109.2, 104.6, 60.1, 56.0, 54.2, 53.5, 41.0; m/z (ES+) 713 (M+H, 100).

Example 4—Synthesis of non-symmetrical 1,4-di-substituted-5,8-dihydroxy-anthraquinones (Formula (I))

The following specific compounds were synthesized:

Example 4a 1-(5,5-Dimethoxypentylamino)-4-(2-(dimethylamino)ethylamino)-5,8-dihydroxyanthracene-9,10-dione (BST-107)

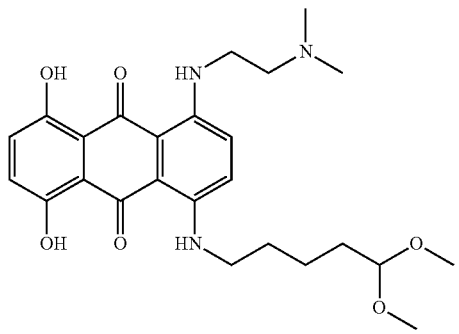 [SMILES: COC(CCCCNc1ccc(NCCN(C)C)c2c1C(=O)c1c(O)ccc(O)c1C2=O)OC]

To a stirred solution of 1-(2-(dimethylamino)ethylamino)-4-fluoro-5,8-dihydroxyanthracene-9,10-dione (60 mg, 0.17 mmol) in pyridine (1 mL) was added 5,5-dimethoxypentan-1-amine (102.61 mg, 0.7 mmol) and the resulting solution was stirred at 70° C. for 6 h. The solvent was evaporated under reduced pressure and the reaction mixture was purified by flash chromatography using gradient eluent (CH₃OH:CH₂Cl₂, 1:99→6:94) to yield the title compound as a dark blue powder (40 mg, 49%). $\delta_H$ (CDCl₃, 400 MHz) 13.3 (2H, brs, OH), 10.3 (2H, br s, NH), 7.16-6.96 (4H, m), 4.32 (1H, t, J 5.5 Hz), 3.45 (2H, t, J 6.5 Hz), 3.21 (6H, s), 2.74 (2H, t, J 6.5 Hz), 2.45 (6H, s), 1.74-1.42 (6H, m); $\delta_C$ (CDCl₃, 100 MHz) 185.6, 185.2, 155.5, 155.46, 146.6, 145.9, 125.0, 124.8, 123.9, 123.7, 115.3, 115.2, 109.4, 108.8, 104.4, 57.7, 52.9, 45.0, 42.9, 40.2, 32.2, 29.4, 22.2; m/z (ES+) 472 (M+H, 100).

Example 4b

N-(2,2-Dimethoxyethyl)-3-(4-(2-(dimethylamino)ethylamino)-5,8-dihydroxy-9,10-dioxo-9,10-dihydroanthracen-1-ylamino)propanamide (BST-108)

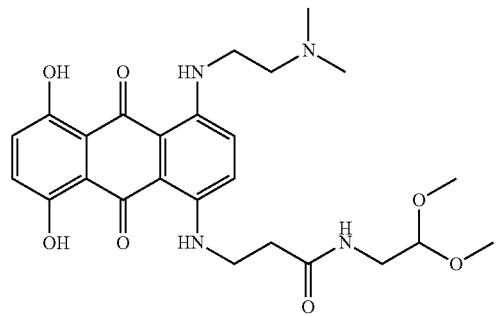 [SMILES: COC(CNC(=O)CCNc1ccc(NCCN(C)C)c2c1C(=O)c1c(O)ccc(O)c1C2=O)OC]

To a stirred solution of 1-(2-(dimethylamino)ethylamino)-4-fluoro-5,8-dihydroxyanthracene-9,10-dione (60 mg, 0.17 mmol) in pyridine (1 mL) was added 3-amino-N-(2,2-dimethoxyethyl)propanamide (123 mg, 0.7 mmol) and the resulting solution was stirred at 70° C. for 6 h. The solvent was evaporated under reduced pressure and the reaction mixture was purified by flash chromatography using gradient eluent (CH₃OH CH₂Cl₂, 1:99→6:94) to yield the title compound as a dark blue powder (79 mg, 90%). $\delta_H$ (CDCl₃, 400 MHz) 13.3 (2H, brs, OH), 10.1 (2H, br s, NH), 6.93 (2H, d, J 6.0 Hz), 6.82 (2H, t, J 6.0 Hz), 6.23 (1H, br s, NH), 4.37 (1H, t, J 5.7 Hz), 3.45 (2H, t, J 6.5 Hz), 3.41 (2H, t, J 5.2 Hz), 3.31 (6H, s), 2.64 (2H, t, J 6.5 Hz), 2.52 (2H, t, J 5.2 Hz), 2.33 (6H, s); $\delta_C$ (CDCl₃, 100 MHz) 184.9, 184.8, 170.6, 155.3, 155.2, 146.1, 145.9, 124.7, 124.5, 123.6, 123.3, 115.2, 115.1, 108.9, 108.7, 102.5, 58.1, 54.3, 45.5, 41.1, 40.8, 39.2, 36.5; m/z (ES+) 501 (M+H, 100).

Example 4c

N-(2-(4-(2-(Dimethylamino)ethylamino)-5,8-dihydroxy-9,10-dioxo-9,10-dihydroanthracen-1-ylamino)ethyl)-3,3-dimethoxypropanamide (BST-111)

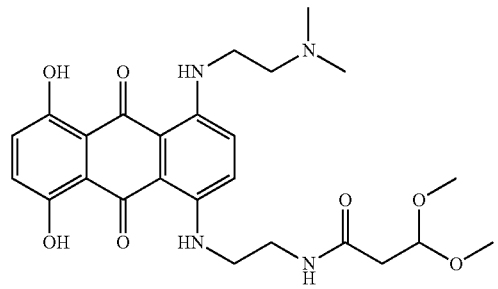 [SMILES: COC(CC(=O)NCCNc1ccc(NCCN(C)C)c2c1C(=O)c1c(O)ccc(O)c1C2=O)OC]

To a stirred solution of 1-(2-(dimethylamino)ethylamino)-4-fluoro-5,8-dihydroxyanthracene-9,10-dione (54 mg, 0.16 mmol) in pyridine (1 mL) was added N-(2-aminoethyl)-3,3-dimethoxypropanamide (111 mg, 0.63 mmol) and the resulting solution was stirred at 70° C. for 6 h. The solvent was evaporated under reduced pressure and the reaction mixture was purified by flash chromatography using gradient eluent (CH$_3$OH:CH$_2$Cl$_2$, 1:99→5:95) to yield the title compound as a dark blue powder (45 mg, 60%). δ$_H$ (CDCl$_3$, 400 MHz) 13.3 (2H, br s, OH), 10.2 (2H, br s, NH), 6.92 (2H, t, J 5.9 Hz), 6.82 (2H, t, J 5.9 Hz), 6.2 (1H, br s, NH), 4.62 (1H, t, J 5.5 Hz), 3.47 (2H, q, J 6.4 Hz), 3.41 (2H, t, J 5.5 Hz), 3.33 (6H, s), 2.63-2.54 (4H, m), 2.52 (2H, t, J 5.5 Hz), 2.27 (6H, s); δ$_C$ (CDCl$_3$, 100 MHz) 184.8, 184.5, 169.8, 169.2, 155.2, 155.1, 146.2, 124.5, 124.2, 123.6, 123.4, 115.2, 115.1, 108.8, 108.5, 102.2, 58.1, 51.4, 45.5, 40.8, 40.8, 37.0, 36.8; m/z (ES+) 501 (M+H, 100).

Example 4d 1-((2-((2,2-dimethoxyethyl)amino)ethyl)amino)-4-((2-(dimethylamino)ethyl)amino)-5,8-dihydroxyanthracene-9,10-dione (BST-302)

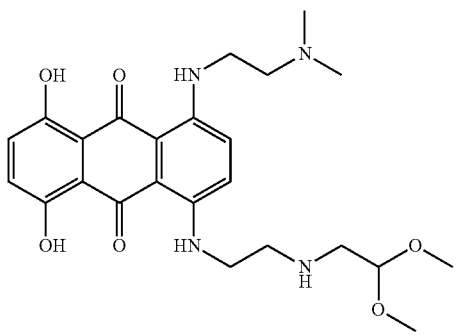 [SMILES: COC(CNCCNc1ccc(NCCN(C)C)c2c1C(=O)c1c(O)ccc(O)c1C2=O)OC]

To a stirred solution of 1-(2-(dimethylamino)ethylamino)-4-fluoro-5,8-dihydroxyanthracene-9,10-dione (30 mg, 0.09 mmol) in pyridine (1 mL) was added N-(2,2-dimethoxyethyl)ethane-1,2-diamine (125 mg, 0.84 mmol) and the resulting solution was stirred at 70° C. for 2 h. The solvent was evaporated under reduced pressure and the reaction mixture was purified by flash chromatography using gradient eluent (CH$_3$OH:CH$_2$Cl$_2$, 1:99→4:9) to yield the title compound as a dark blue powder (37 mg, 90%). δ$_H$ (CDCl$_3$, 400 MHz) 13.36 (2H, s), 10.25 (1H, t, J 5H), 10.22 (1H, t, J 5H), 6.97 (2H, s), 6.89 (2H, s), 4.43 (1H, t, J 5 Hz), 3.34 (10H, m), 2.91 (2H, t, J 6 Hz), 2.75 (2H, d, J 6 Hz), 2.58 (2H, t, J 6 Hz), 2.26 (6H, s); δ$_C$ (CDCl$_3$, 101 MHz) 185.29, 184.93, 155.29, 146.30, 146.21, 124.52, 124.43, 123.58, 123.55, 115.38, 108.96, 108.84, 103.92, 58.32, 54.15, 51.02, 50.62, 45.62, 42.96, 41.11; m/z (ES+) 473 (M+H, 100); Anal. calculated for C$_{24}$H$_{32}$N$_4$O$_6$: C, 61.04; H, 6.83; N, 11.86. Found: C, 61.15; H, 6.78; N, 11.81.

Example 4e 1-((3-((2,2-dimethoxyethyl)amino)propyl)amino)-4-((2-(dimethylamino)ethyl)amino)-5,8-dihydroxyanthracene-9,10-dione (BST-303)

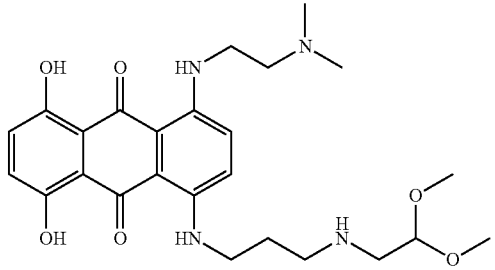 [SMILES: COC(CNCCCNc1ccc(NCCN(C)C)c2c1C(=O)c1c(O)ccc(O)c1C2=O)OC]

To a stirred solution of 1-(2-(dimethylamino)ethylamino)-4-fluoro-5,8-dihydroxyanthracene-9,10-dione (30 mg, 0.09 mmol) in pyridine (1 mL) was added N-(2,2-dimethoxyethyl)propane-1,3-diamine (129 mg, 0.80 mmol) and the resulting solution was stirred at 70° C. for 2 h. The solvent was evaporated under reduced pressure and the reaction mixture was purified by flash chromatography using gradient eluent (CH$_3$OH:CH$_2$Cl$_2$, 1:99→4:9) to yield the title compound as a dark blue powder (34 mg, 70%). δ$_H$ (CDCl$_3$, 400 MHz) 13.45 (1H, s), 13.35 (1H, s), 10.27 (1H, t, J 5H), 10.23 (1H, t, J 5H), 6.96 (2H, s), 6.89 (2H, s), 4.48 (1H, t, J 5 Hz), 3.32 (10H, m), 2.74 (2H, t, J 6 Hz), 2.70 (2H, d, J 6 Hz), 2.58 (2H, t, J 6 Hz), 2.28 (6H, s), 1.83 (2H, m, J 6 Hz); δ$_C$ (CDCl$_3$, 101 MHz) 184.83, 155.30, 155.24, 146.43, 146.21, 124.40, 124.35, 123.60, 123.55, 115.44, 108.75, 108.68, 103.89, 58.36, 54.09, 51.27, 47.33, 45.66, 41.17, 40.93, 29.97; m/z (ES+) 487 (M+H, 100); Anal. calculated for C$_{25}$H$_{34}$N$_4$O$_6$: C, 61.75; H, 7.04; N, 11.51. Found: C, 60.76; H, 7.50; N, 11.14.

Example 4f 1-((4-((2,2-dimethoxyethyl)amino)butyl)amino)-4-((2-(dimethylamino)ethyl)amino)-5,8-dihydroxyanthracene-9,10-dione (BST-304)

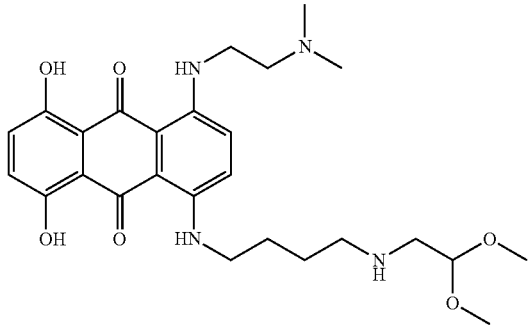 [SMILES: COC(CNCCCCNc1ccc(NCCN(C)C)c2c1C(=O)c1c(O)ccc(O)c1C2=O)OC]

To a stirred solution of 1-(2-(dimethylamino)ethylamino)-4-fluoro-5,8-dihydroxyanthracene-9,10-dione (41 mg, 0.12 mmol) in pyridine (1 mL) was added N-(2,2-dimethoxyethyl)butane-1,4-diamine (140 mg, 0.79 mmol) and the resulting solution was stirred at 70° C. for 2 h. The solvent was evaporated under reduced pressure and the reaction mixture was purified by flash chromatography using gradient eluent (CH$_3$OH:CH$_2$Cl$_2$, 1:99→4:9) to yield the title compound as a dark blue powder (46 mg, 92%). δ$_H$ (CDCl$_3$, 400 MHz) 13.42 (1H, s), 13.35 (1H, s), 10.24 (1H, t, J 5H), 10.18 (1H, t, J 5H), 6.97 (2H, s), 6.85 (2H, s), 4.41 (1H, t, J 5.2 Hz), 3.32 (10H, m), 3.22 (2H, q, J 5.2 Hz), 2.68 (2H, d, J 5.2 Hz), 2.64 (2H, t, J 7.2 Hz), 2.56 (2H, t, J 7.2 Hz), 2.27 (6H, s), 1.68 (2H, m), 1.57 (2H, m); δ$_C$ (CDCl$_3$, 101 MHz) 184.82, 184.75, 155.28, 155.23, 146.36, 146.17, 124.35, 124.32, 123.60, 123.46, 115.44, 108.75, 108.60, 103.91, 58.36, 54.06, 51.25, 49.56, 45.67, 42.87, 41.16, 27.66, 27.30; m/z (ES+) 501 (M+H, 100). Anal. calculated for C$_{26}$H$_{36}$N$_4$O$_6$: C, 62.42; H, 7.25; N, 11.20. Found: C, 61.99; H, 7.64; N, 10.99.

Example 4g 1-((5-((2,2-dimethoxyethyl)amino)pentyl)amino)-4-((2-(dimethylamino)ethyl)amino)-5,8-dihydroxyanthracene-9,10-dione (BST-305)

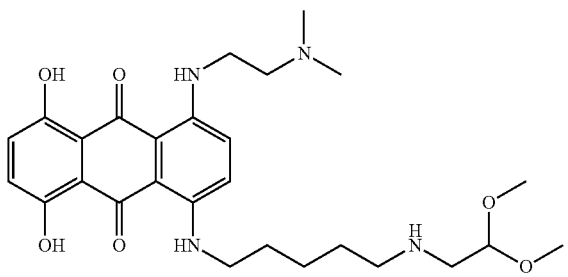 [SMILES: COC(CNCCCCCNc1ccc(NCCN(C)C)c2c1C(=O)c1c(O)ccc(O)c1C2=O)OC]

To a stirred solution of 1-(2-(dimethylamino)ethylamino)-4-fluoro-5,8-dihydroxyanthracene-9,10-dione (30 mg, 0.09 mmol) in pyridine (1 mL) was added N-(2,2-dimethoxyethyl)pentane-1,5-diamine (122 mg, 0.64 mmol) and the resulting solution was stirred at 70° C. for 2 h. The solvent was evaporated under reduced pressure and the reaction mixture was purified by flash chromatography using gradient eluent (CH$_3$OH:CH$_2$Cl$_2$, 1:99→4:9 to yield the title compound as a dark blue powder (39 mg, 76%). $\delta_H$ (CDCl$_3$, 400 MHz) 13.40 (1H, s), 13.33 (1H, s), 10.21 (1H, t, J 5H), 10.14 (1H, t, J 5H), 6.95 (2H, s), 6.80 (2H, m), 4.39 (1H, t, J 5.2 Hz), 3.31 (10H, m), 3.16 (2H, m), 2.67 (2H, d, J 5.2 Hz), 2.58 (4H, m), 2.27 (6H, s), 1.66 (2H, m), 1.51 (2H, m), 1.42 (2H, m); $\delta_C$ (CDCl$_3$, 101 MHz) 184.65, 184.57, 155.22, 155.15, 146.36, 146.13, 124.18, 123.53, 123.39, 115.45, 115.44, 108.61, 108.43, 103.90, 58.34, 54.02, 51.27, 49.89, 49.82, 45.66, 42.86, 41.12, 29.86, 29.40, 24.86; m/z (ES+) 515 (M+H, 100). Anal. calculated for C$_{27}$H$_{38}$N$_4$O$_6$: C, 63.06; H, 7.45; N, 10.89. Found: C, 62.02; H, 7.18; N, 10.45.

Example 4h 1-((6-((2,2-dimethoxyethyl)amino)hexyl)amino)-4-((2-(dimethylamino)ethyl)amino)-5,8-dihydroxyanthracene-9,10-dione (BST-301)

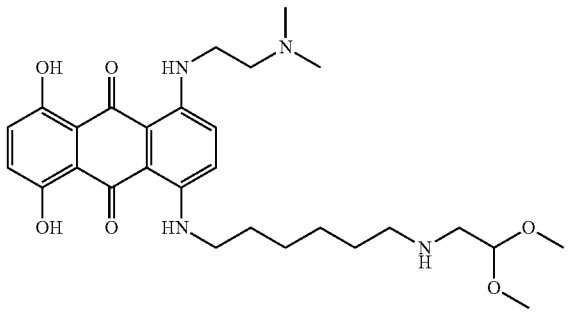 [SMILES: COC(CNCCCCCCNc1ccc(NCCN(C)C)c2c1C(=O)c1c(O)ccc(O)c1C2=O)OC]

To a stirred solution of 1-(2-(dimethylamino)ethylamino)-4-fluoro-5,8-dihydroxyanthracene-9,10-dione (30 mg, 0.09 mmol) in pyridine (1 mL) was added N-(2,2-dimethoxyethyl)hexane-1,6-diamine (103 mg, 0.51 mmol) and the resulting solution was stirred at 70° C. for 2 h. The solvent was evaporated under reduced pressure and the reaction mixture was purified by flash chromatography using gradient eluent (CH$_3$OH:CH$_2$Cl$_2$, 1:99→4:9 to yield the title compound as a dark blue powder (30 mg, 63%). $\delta_H$ (CDCl$_3$, 400 MHz) 13.43 (1H, s), 13.39 (1H, s), 10.32 (1H, t, J 5H), 10.26 (1H, t, J 5H), 7.01 (2H, s), 6.99 (2H, d, J 1.6 Hz), 4.40 (1H, t, J 5.6 Hz), 3.38 (2H, q, J 1.6 Hz), 3.32 (6H, s), 3.27 (2H, q, J 1.6 Hz), 2.67 (2H, d, J 5.6 Hz), 2.57 (4H, m), 2.28 (6H, s), 1.68 (2H, m), 1.46 (4H, m), 1.37 (3H, m); $\delta_C$ (CDCl$_3$, 101 MHz) 185.10, 185.08, 155.41, 155.34, 146.55, 146.25, 124.59, 123.78, 123.67, 115.47, 115.44, 108.99, 108.80, 103.92, 58.40, 54.03, 51.28, 49.91, 45.66, 42.96, 41.23, 30.02, 29.49, 27.05, 27.03; m/z (ES+) 529 (M+H, 100); Anal. calculated for C$_{28}$H$_{40}$N$_4$O$_6$: C, 63.66; H, 7.63; N, 10.60. Found: C, 62.05; H, 7.45; N, 10.80.

Example 4i 1-((2,2-dimethoxyethyl)amino)-4-((2-(dimethylamino)ethyl)amino)-5,8-dihydroxyanthracene-9,10-dione (BST-203)

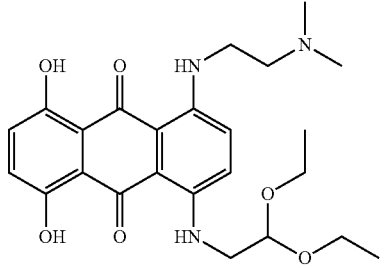 [SMILES: CCOC(CNc1ccc(NCCN(C)C)c2c1C(=O)c1c(O)ccc(O)c1C2=O)OCC]

To a stirred solution of 1-(2-(dimethylamino)ethylamino)-4-fluoro-5,8-dihydroxyanthracene-9,10-dione (35 mg, 0.10 mmol) in pyridine (1 mL) was added 2,2-dimethoxyethanamine (120 mg, 1.14 mmol) and the resulting solution was stirred at 90° C. for 1 h. The solvent was evaporated under reduced pressure and the reaction mixture was purified by flash chromatography using gradient eluent (CH$_3$OH:CH$_2$Cl$_2$, 1:99→5:95) to yield the title compound as a dark blue powder (27 mg, 63%). $\delta_H$ (CDCl$_3$, 400 MHz) 13.45 (1H, s, OH), 13.42 (1H, s, OH), 10.38 (1H, t, NH, J 5 Hz), 10.32 (1H, t, NH, J 5 Hz), 7.13 (1H, d, J 10 Hz), 7.07 (1H, d, J 10 Hz), 7.05 (2H, s), 4.69 (1H, t, J 5 Hz), 3.72 (2H, m), 3.58 (2H, m), 3.46 (2H, t, J 5.5), 3.41 (2H, q, J 5.5), 2.59 (2H, t, J 5.5), 2.28 (6H, s), 1.20 (6H, t, J 6); $\delta_C$ (CDCl$_3$, 100 MHz) 185.72, 185.48, 155.51, 155.49, 146.42, 146.23, 125.05, 124.89, 124.11, 123.67, 115.35, 109.49, 109.15, 101.20, 62.96, 58.34, 45.73, 41.22, 15.42; m/z (ES+) 458 (M+H, 100).

Example 5—Synthesis of Symmetrical 1,5-di-substituted-anthraquinones (Formula (II))

The following specific compound was synthesized:

Example 5a 1,5-bis((5,5-dimethoxypentyl)amino)anthracene-9,10-dione (BST-401)

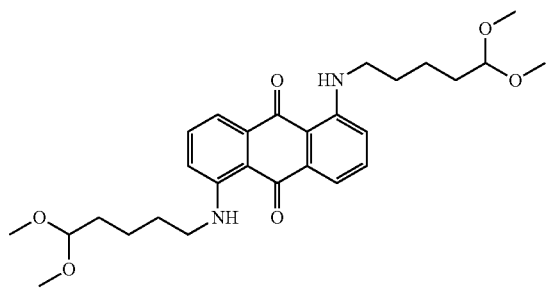

To a stirred solution of 1,5-dichloroanthraquinone (50 mg, 0.18 mmol) in pyridine (2 mL) was added of 5,5-dimethoxypentan-1-amine (725 mg, 1.80 mmol) and the resulting solution was stirred at 90° C. for 96 hours. The solvent was evaporated under reduced pressure and the reaction mixture was purified by flash chromatography using gradient eluent (CH$_3$OH:CH$_2$Cl$_2$, 0:100→40:90) to yield the title compound as a purple solid (15.7 mg, 17.5%). $\delta_H$ (CDCl$_3$, 400 MHz)) δ 9.64 (t, J=4.8 Hz, 2H, NH$_2$), 7.46 (m, 4H, Ar—H), 6.88 (d, J=6.4 Hz, 2H, Ar—H), 4.32 (t, J=5.6 Hz, 2H, CH), 3.26 (s, 12H, OCH$_3$), 3.24 (m, 4H, NHCH$_2$), 1.71 (m, 4H, NHCH$_2$CH$_2$CH$_2$CH$_2$CH), 1.62 (m, 4H, NHCH$_2$CH$_2$CH$_2$CH$_2$CH), 1.51 (m, 4H, NHCH$_2$CH$_2$CH$_2$CH$_2$CH); $\delta_C$ (CDCl$_3$, 101 MHz) δ 185.47, 151.46, 136.31, 135.25, 116.37, 114.68, 112.88, 104.36, 52.84, 42.84, 32.26, 28.99, 22.34. HRMS Found 499.2796, C$_{28}$H$_{38}$N$_2$O$_6$ req. 499.2803.

Example 6—Synthesis of Symmetrical 1,8 di-substituted-anthraquinones (Formula (IV))

The following specific compound was synthesized:

Example 6a 1,8-bis((5,5-dimethoxypentyl)amino)anthracene-9,10-dione (BST-400)

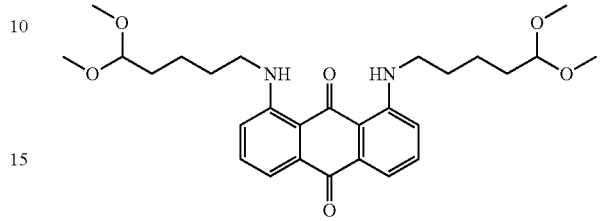

To a stirred solution of 1,8-dichloroanthraquinone (50 mg, 0.18 mmol) in pyridine (2 mL) was added of 5,5-dimethoxypentan-1-amine (726 mg, 1.80 mmol) and the resulting solution was stirred at 90° C. for 72 hours. The solvent was evaporated under reduced pressure and the reaction mixture was purified by flash chromatography using gradient eluent (CH$_3$OH:CH$_2$Cl$_2$, 0:100→40:90) to yield the title compound as a purple solid (22.4 mg, 25%). $\delta_H$ (CDCl$_3$, 400 MHz) δ 9.54 (t, J=4.8 Hz, 2H, NH$_2$), 7.46 (d, J=6.8 Hz, 2H, Ar—H), 7.43-7.36 (m, 2H, Ar—H), 6.94 (d, J=8.3 Hz, 2H, Ar—H), 4.35 (t, J=5.6 Hz, 2H, CH), 3.27 (s, 12H, OCH$_3$), 3.26-3.22 (m, 4H, NHCH$_2$), 1.73 (dt, J=14.8, 7.5 Hz, 4H, NHCH$_2$CH$_2$CH$_2$CH$_2$CH), 1.64 (dd, J=15.3, 6.0 Hz, 4H, NHCH$_2$CH$_2$CH$_2$CH$_2$CH), 1.51-1.42 (m, 4H, NHCH$_2$CH$_2$CH$_2$CH$_2$CH); $\delta_C$ (CDCl$_3$, 101 MHz) δ 189.04 & 184.73, 151.13, 134.36, 134.14, 117.64, 114.88, 114.34, 104.33, 52.78, 42.99, 32.25, 29.04, 22.35. HRMS Found 499.2799, C$_{28}$H$_{38}$N$_2$O$_6$ req. 499.2803.

Example 7—Synthesis of Symmetrical 2,6-di-substituted-anthraquinones (Formula (III))

The following specific compound can be synthesized under the same conditions described above for BST-400 but using 2,6-dichloroanthraquinone as starting material:

Example 7a 2,6-bis((5,5-dimethoxypentyl)amino)anthracene-9,10-dione (BST-402)

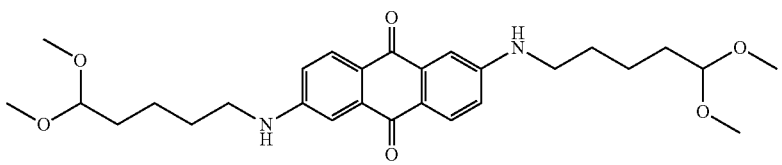

To a stirred solution of 2,6-dichloroanthraquinone (50 mg, 0.18 mmol) in pyridine (2 mL) was added of 5,5-dimethoxypentan-1-amine (726 mg, 1.80 mmol) and the resulting solution was stirred at 90° C. for 72 hours. The solvent was evaporated under reduced pressure and the reaction mixture was purified by flash chromatography using gradient eluent (CH$_3$OH:CH$_2$Cl$_2$, 0:100→10:90) to yield the title compound.

Testing of the Compounds
A. Absorption and Fluorescence Spectra

The compounds were exited at 540 nm and at the wavelength of their absorption peak 1 (λ1 nm). The far-red fluorescent DNA dye DRAQ5 was used as reference.

Materials and Methods for the Determination of the Fluorescence Excitation and Emission Characteristics of Compounds Compounds were dissolved in DMSO (Sigma) to 20 mM stock concentration. DRAQ5 (Biostatus Ltd) was used as a control anthraquinone agent dissolved in deionised water. Working solutions were prepared in PBS (phosphate buffered saline; Sigma) or HEPES (4-(2-hydroxyethyl)-1-piperazineethanesulfonic acid; Sigma) at 20 or 40 µM. Probe solutions (20 µM), respectively in PBS or HEPES, were pipetted into a 1 mL quartz cuvette (Thermo Fisher Scientific). After obtaining baseline spectra in relevant buffer to zero the instrument, absorbance measurements were obtained using a Beckmann Coulter DU 800 UV/Visible spectrophotometer. The excitation wavelengths were scanned from 280 to 800 nm. Fluorescent spectral scans were performed using a Perkin Elmer LS-50B Luminescence spectrophotometer. To obtain emission scans, the excitation wavelength was set accordingly to the maximum values for each agent or another designated excitation wavelength that matches typical laser lines; and the emission wavelength were scanned from 400 nm to 900 nm in 1 nm increments. A Xenon flash lamp was used as the light source, with the lamp energy set to high. For each data point ten measurements were acquired with the photomultiplier tube sensitivity set at 125.

Figure 1B:
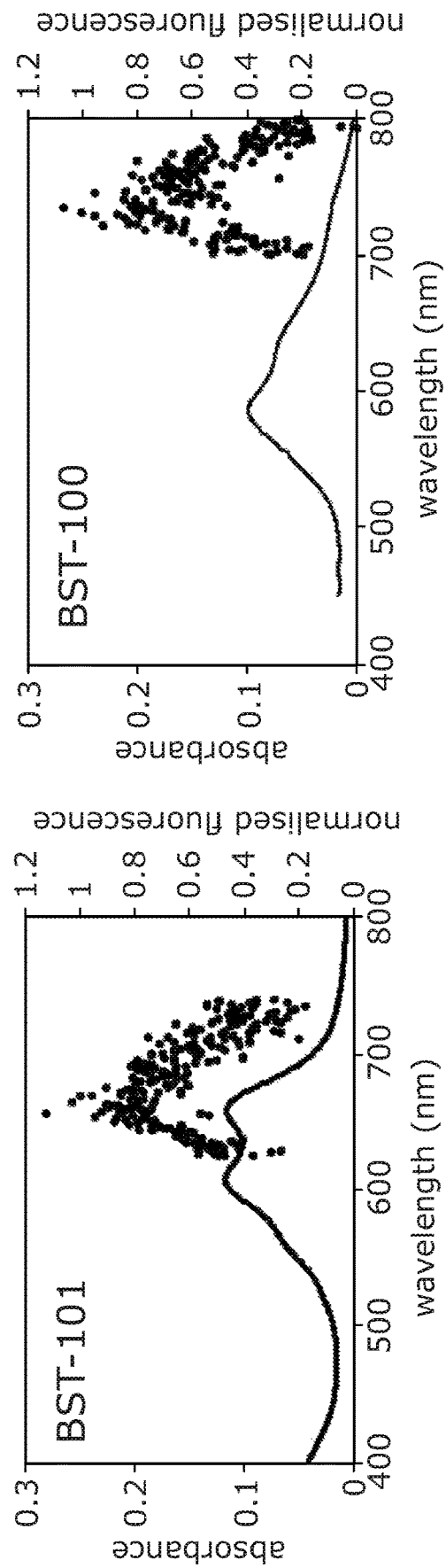
Figure 1B:
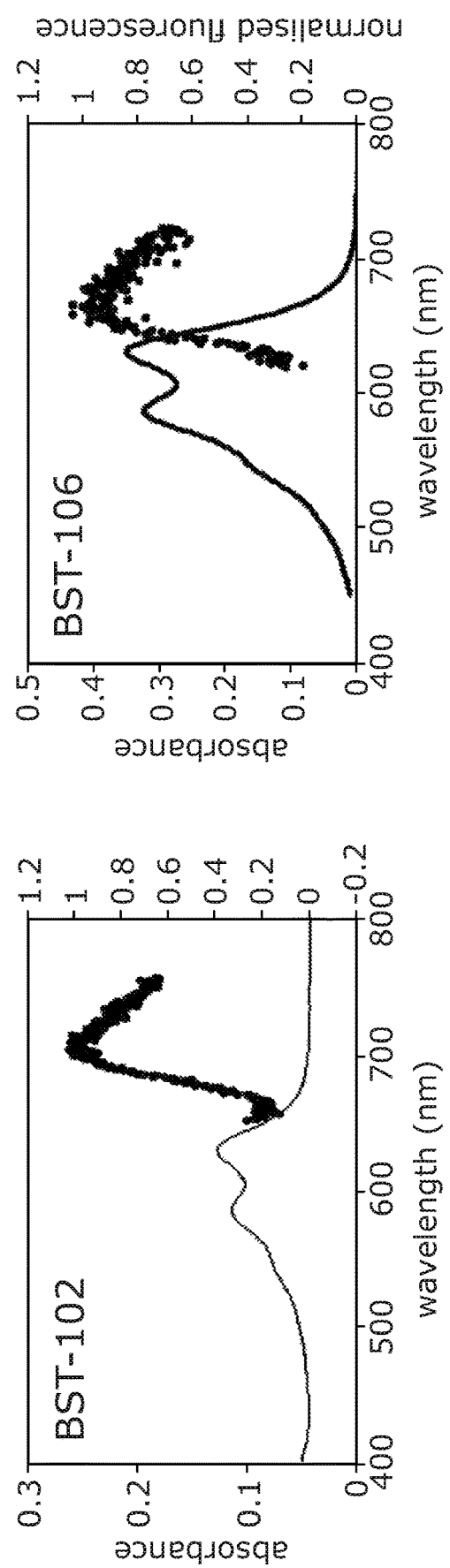

Typical absorption spectra and fluorescence spectra of compounds BST-108, BST-109, BST-110 and BST-111 and BST-100, BST-101 and BST-106 can be seen in FIG. 1A and FIG. 1B respectively.

Compounds were excited at a wavelength corresponding to the first absorbance peak 1 (FIG. 1A and FIG. 1B show absorption (line) and fluorescence (dots) spectra of compounds; both are normalised to peak value.

The absorption and fluorescence spectra show that the compounds of the invention have absorption and emission in the long-wavelength spectral region (>650 am).

Table 1 shows the summarised fluorescence emission data for tested compounds in PBS and HEPES.

TABLE 1

| Compound | λ1 nm (Ex in PBS) | 540 nm (Ex in PBS) | λ1 nm (Ex in HEPES) |
|---|---|---|---|
| DRAQ5 | >665 | 635 | >665 |
| BST-104 | 684 | 712 | 726 |
| BST-108 | 685 | 692 | 684 |
| BST-111 | 684 | 684 | 684 |
| BST-200 | 688 | 690 | 684 |
| BST-201 | 690.5 | 684 | 684 |
| BST-202 | — | — | 680 |
| BST-203 | 678 | 690 | 696 |
| BST-100 | 747.5 | — | 740 |
| BST-101 | — | 712 | — |
| BST-102 | 661 | 670 | 663 |
| BST-106 | 660 | 670 | 664 |
| BST-109 | 666 | 660 | 660 |
| BST-110 | 665.5 | 662 | 660 |

B. DNA Affinity

DNA melting temperature (variation in Tm) was used to assess interaction between CT-DNA and compounds of Formula (I). Studies were carried out using a thermal DNA denaturation assay.

Materials and Methods for the Assessment of DNA-Binding Affinity Via DNA Melting Studies Using Calf Thymus DNA (CT-DNA)

Melting curve assays for DNA binding analysis of compounds were constructed as follows:

CT-DNA melting buffer was prepared by making up a 1 L solution A of (10 mM $NaH_2PO_4$ and 1 mM $Na_2EDTA$) and a separate 1 L solution B (10 mM $Na_2HPO_4$ and 1 mM $Na_2EDTA$), and then solution A was added to solution B until pH 7.0 was achieved. Calf thymus DNA (CT-DNA, Sigma) solutions were prepared for use by dissolving 21-23 mg in 20 mL of the CT-DNA melting buffer and stored at 4° C. Mitoxantrone (Sigma) was solubilized in DMSO, diluted to desired concentrations in 10 mM Tris-HCl buffer (pH 7.4) and used as control. Its concentration was determined spectrophotometrically using a molar extinction coefficient of 8,360 $M^{-1}$ $cm^{-1}$ at 608 nm (Enache, M. and Volanschi, E. 2010. Spectral characterisation of self-association of antitumor drug mitoxantrone Revue Roumaine De Chimie 55(4), pp. 255-+).

The CT-DNA thermal melting assay mixtures were prepared by adding sufficient CT-DNA stock solution to CT-DNA melting buffer, to ensure the preparation of a 50 µM CT-DNA solution. Compound stock solution was then added to the 50 µM CT-DNA solution, to ensure the final concentration of compound in the mixture was 10 µM.

All UV absorbance experiments were conducted on a Cary 400Bio Spectrophotometer (Varian, Agilent) equipped with a Peltier Temperature Controller. This was attached to a Cary Thermostatable Multicell Block, to provide stable, continuous temperature control. A pair of masked quartz 1.2 mL microcells cells with a 4 mm width, and 10 mm path length was used for all absorbance studies. 1.2 mL of CT-DNA melting buffer was added to the reference cuvette and 1.2 mL of DNA-anthraquinone mixture was added to the reaction cuvette. Absorbance versus temperature profiles were measured at 260 nm with melting temperature (Tm) measurements initiated at 40° C. The temperature of the test solution was increased at 1° C./min till 95° C. was reached. Melting curves generated by computer software were printed out and the melting points were determined using the published graphical method by Brown and Fox (1997; Brown, P. M. and Fox, K. R. 1997. Foot-printing studies with nucleosome-bound DNA. Methods in Molecular Biology; Drug-DNA interaction protocols. Vol. 90. pp. 81-93). The Tm was the mean of two separate determinations within 0.2° C.

The assay was performed initially by incubating 50 µM of calf thymus DNA (CT-DNA), in the presence of 10 µM of mitoxantrone, to validate the assay and to have a positive control for comparison. 10 µM solutions of compound counterparts were incubated with 50 µM CT-DNA.

Table 2 shows results of CT-DNA/compound Formula (I) melting temperatures before and after acidic hydrolysis.

TABLE 2

| Compound | Compound Tm (° C.) | Hydrolysed product of compound Tm (° C.) |
|---|---|---|
| Mitoxantrone | >95 | — |
| BST-101 | 69.0 | 69.7 |
| BST-107 | 74.0 | 71.9 |
| BST-102 | 69.0 | 70.0 |
| BST-103 | 69.4 | 70.1 |
| BST-104 | 69.6 | ** |
| BST-105 | 69.0 | ** |
| BST-106 | 72.1 | * |

TABLE 2-continued

| Compound | Compound Tm (° C.) | Hydrolysed product of compound Tm (° C.) |
|---|---|---|
| BST-108 | 76.4 | * |
| BST-109 | 72.0 | 72.9 |
| BST-110 | 72.0 | 71.6 |
| BST-111 | 71.6 | 74.6 |
| BST-200 | 74.2 | 70.4 |
| BST-201 | 70.8 | * |
| BST-202 | 70.0 | 70.0 |
| BST-203 | 73.0 | 72.6 |

* Excess of interference, hence any calculation of Tm was inaccurate.
** Solubility issues in the working buffer, therefore no experiment was performed.

C. Cell Studies—Labelling and Loading

Methodology: Labelling of Fixed and Live Cells

Cells were seeded in a 24 well coverslip bottomed-plate, cultured overnight in McCoys media. 24 or 48 hours later the cells were washed gently with 3×2 mL PBS per well. The PBS was removed and 0.5 mL of 4% paraformaldehyde solution [a 4% paraformaldehyde solution in PBS was made fresh each time from a 16% stock solution (Thermo Fisher Scientific)] was added in each well and cells were incubated for 30 min. The paraformaldehyde was removed and cells were washed 3×2 mL PBS per well. 1 mL of PBS or HEPES was added to each well.

Before analysis, cells were incubated at 37° C. in the dark for the period designated. Samples were analysed directly without any further washing step. For live cell labelling cells were seeded, plated in a similar way, into a similar multi-well dish for optimal optical performance and could be used across all microscope platforms.

This basic protocol was the standard for testing the patterns of AAQ agents at 20 µM, compared to 20 µM of DRAQ5 as the benchmark reference (both in terms of cellular location and ability to detect the red fluorescence).

a) Labelling—Fixed Cells

Figure 2:
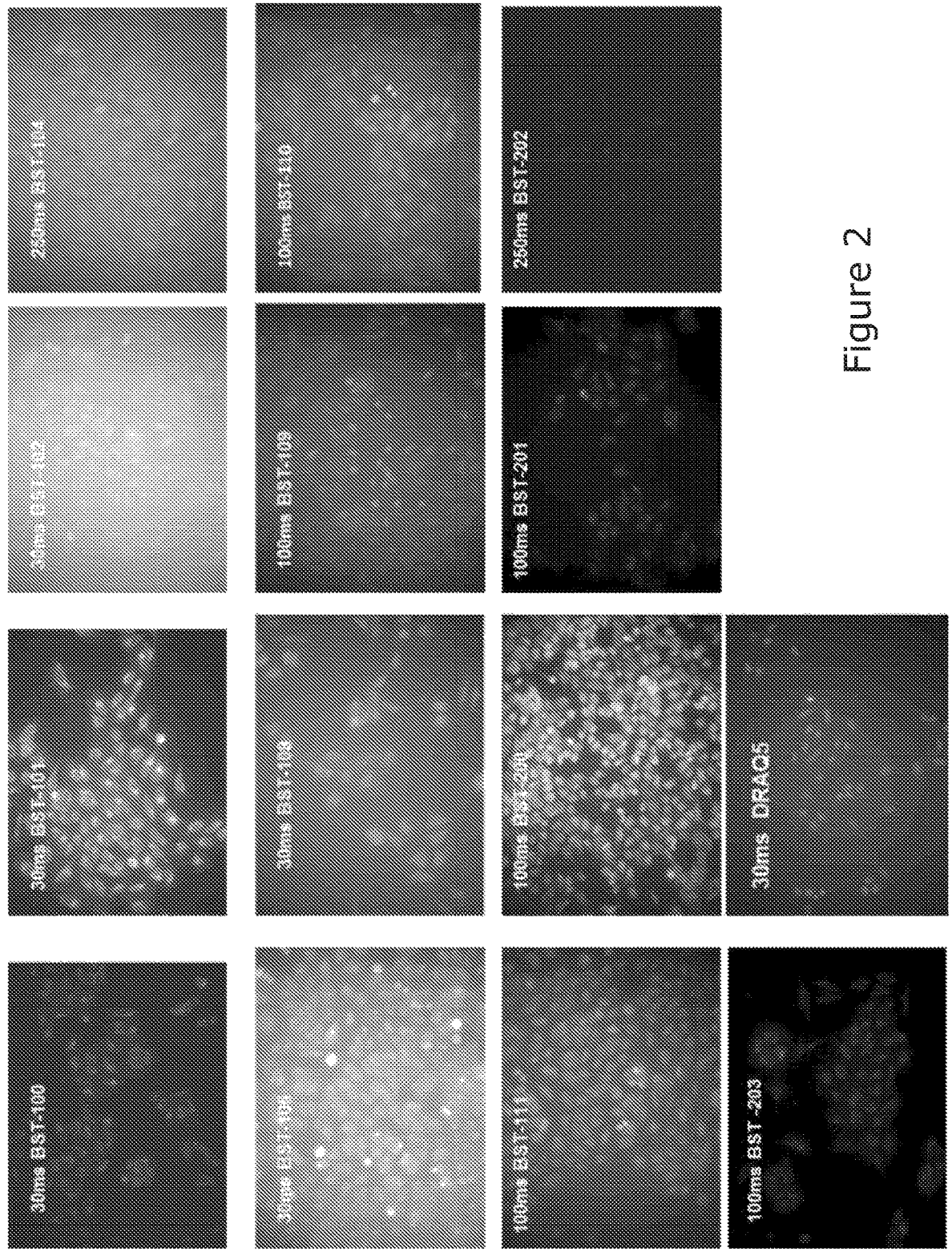
FIG. 2 shows staining of fixed cells. The figure shows fluorescence microscopic images of α-2 OS cells stained for 1 hour with different compounds according to the present invention and with DRAQ5 as a reference.

Low resolution wide-field fluorescence microscopy was used to evaluate cell labelling in fixed human osteosarcoma U-2 OS cells. The system was an Axiovert 100 microscope (Carl Zeiss, Welwyn Garden City, UK) ×10 0.3 NA air objective lens and an ORCA-ER CCD camera (Hamamatsu, Reading, UK). Illumination was controlled by a shutter in front of the transmission lamp. Image capture was controlled using Metamorph software. This evaluates the ability of the compounds to label cellular compartments without active uptake or efflux prohibiting delivery into the given cell. Image collection was performed after 1 h of exposure to probes in PBS. The results are shown in FIG. 2. The calibration bar represents 50 µm.

Compounds BST-101 and BST-106 showed diverse staining when put into cells. BST-101 and BST-106 have a diffuse cytoplasmic staining, with some perinuclear and nucleoli labelling. Moreover, very bright background was observed in BST-106 compared to BST-101.

Compounds BST-108 and BST-109 showed heterogeneity in cytoplasmic staining and positive spots in the nuclei due to DNA binding. Moreover, BST-110 and BST-111 displayed very high background fluorescence, especially in BST-110, with cytoplasmic staining and heterogeneity on labelling of mitotic figures.

A very bright fluorescence was seen for BST-200, with cytoplasmic staining, good object recognition, and some heterogeneity on nuclear staining.

b) Loading—A549 Live Cells

Low resolution wide-field fluorescence microscopy was used to evaluate cell uptake and localisation of the probe compounds. The system was an Axiovert 100 microscope (Carl Zeiss, Welwyn Garden City, UK) ×10 0.3 NA air objective lens and an ORCA-ER CCD camera (Hamamatsu, Reading, UK). Illumination was controlled by a shutter in front of the transmission lamp. Image capture was controlled using Metamorph software. Human non-small cell lung cancer A549 cell line was used as the cell model to determine whether variation of the probe loading and localisation occurred in cell population sustaining a "side population" (SP) (Smith P J, Wiltshire M, Chappell S C, Cosentino L, Burns P A, Pors K, Errington R J. Kinetic analysis of intracellular Hoechst 33342—DNA interactions by flow cytometry: misinterpretation of side population status? Cytometry A 2013; 83:161-9) with a known capacity to efflux xenobiotic molecules, including the DNA dye Hoechst 33342.

Figure 3:
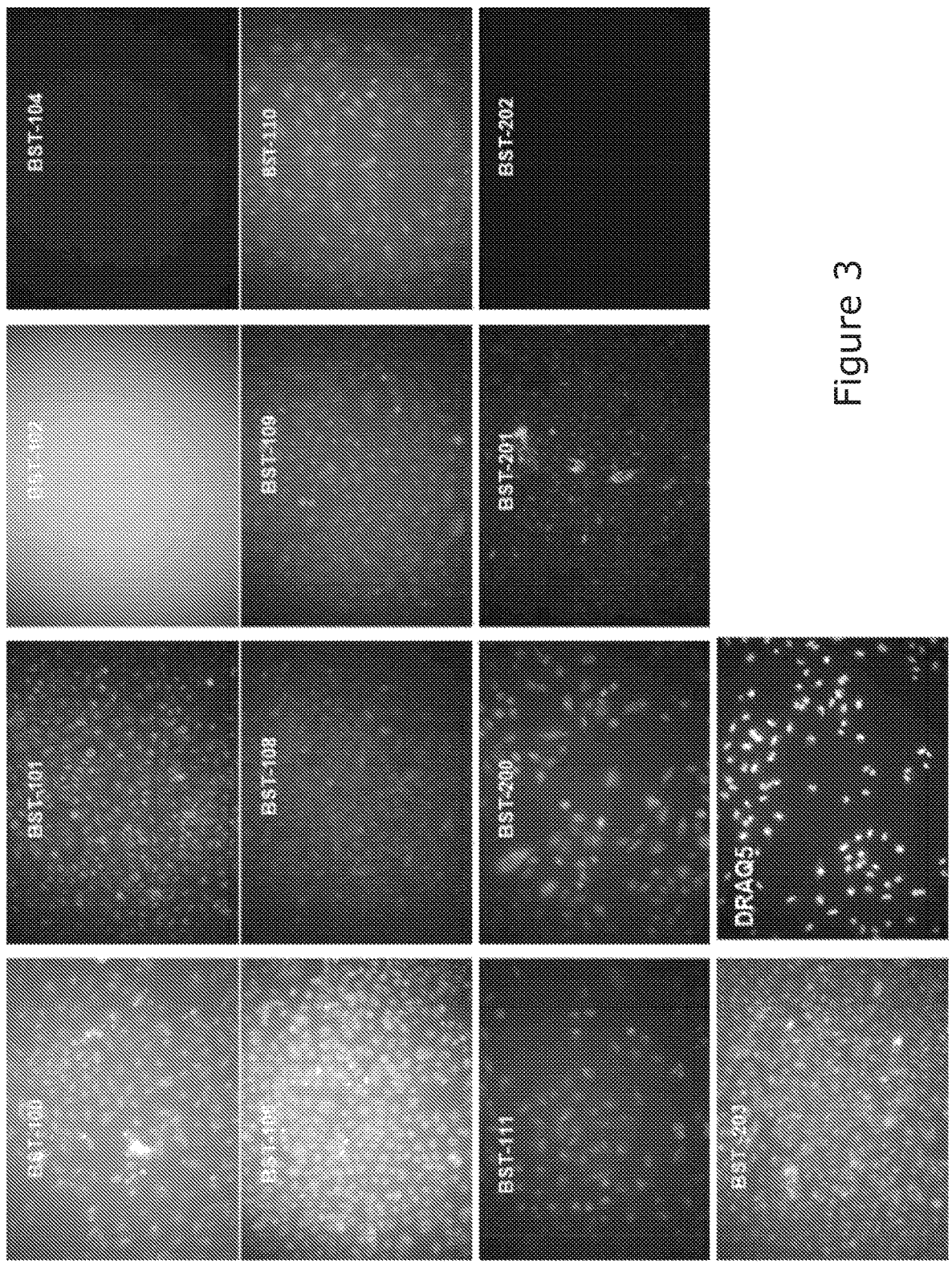
FIG. 3 shows staining of live cells. The figure shows fluorescent microscopic images of A549 cells stained with different compounds according to the present invention and with DRAQ5 as a reference.

Cells were incubated for 30 min with each compound and then images were collected at a 30 ms exposure time using low resolution wide-field fluorescence microscopy. Using an Axiovert 100 microscope (Carl Zeiss, Welwyn Garden City, UK) ×10 0.3 NA air objective lens and an ORCA-ER CCD camera (Hamamatsu, Reading, UK). Illumination was controlled by a shutter in front of the transmission lamp. Image capture was controlled using Metamorph software. The results are shown in FIG. 3. The calibration bar represents 50 µm.

As before, BST-101 and BST-106 showed heterogeneous cytoplasmic staining, with BST-106 in particular displaying a high background. The BST-108, BST-109 and BST-110 analogues revealed very bright cellular fluorescence, whereas BST-111 has a greater contrast and diffuse cellular staining.

BST-200 showed heterogeneity on cytoplasmic load on, with bright fluorescence signal and staining of mitotic figures, whereas BST-201 had perinuclear accumulation.

c) Confocal Laser Scanning Microscopy (CLSM) Analysis in the U-2 OS Cell Line

Confocal laser scanning microscopy (CLSM) was used to analyse the localisation of compounds BST-100, BST-101 and BST-106 with the U-2 OS cells, as it permitted the acquisition of volume limited optical sections through the cell and media. Excitation (637 nm) and emission (>665 nm) values for the probe analysis were the optimal conditions. The data sets obtained were processed and assembled into a single maximum projection image.

The patterns were analysed after 30 min incubation at different z depths and eliminating the solution background. The nucleus/cytoplasm ratio was calculated to quantify the localisation of the probe per cell.

Figure 4:
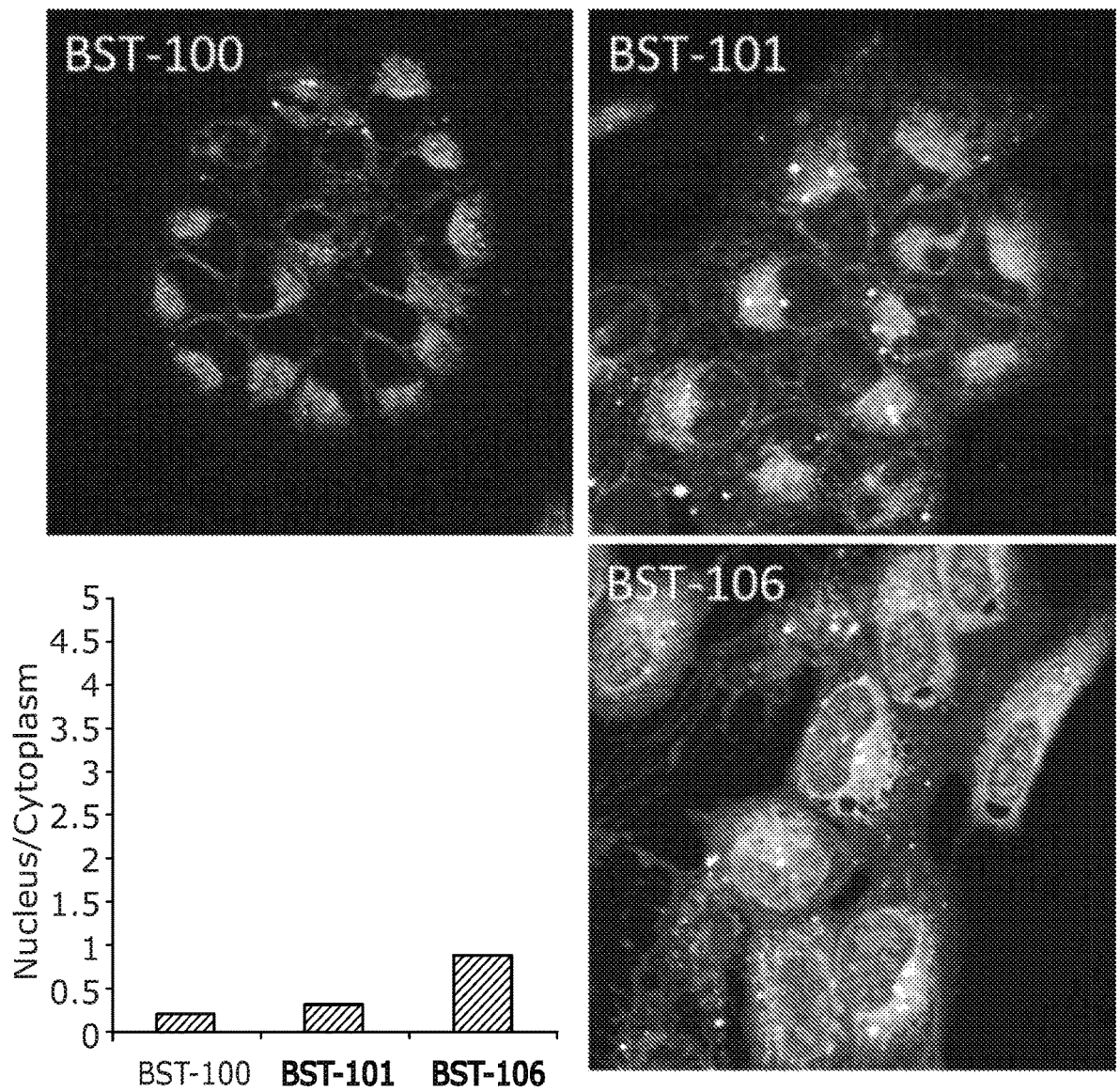
FIG. 4 shows fluorescence analysis via direct confocal imaging of compounds BST-100, BST-101 and BST-106.

The results are shown in FIG. 4. A Radiance CLSM (BioRad Microscience) was used attached to an inverted Nikon microscope. Image acquisition was performed using excitation (637 nm) and emission (>665 nm) wavelengths. The histogram plot reports the nucleus/cytoplasm index to determine DNA binding in live cells. The calibration bar represents 10 µm.

Optical sectioning enabled detection of low levels of probe in the perinuclear region, with probable overload in Golgi body and large vesicles for BST-100 and BST-101. The accumulation area appeared similarly to the MTOC (microtubule organizing centre); however BST-106 gave an additional nuclear signal.

Figure 5:
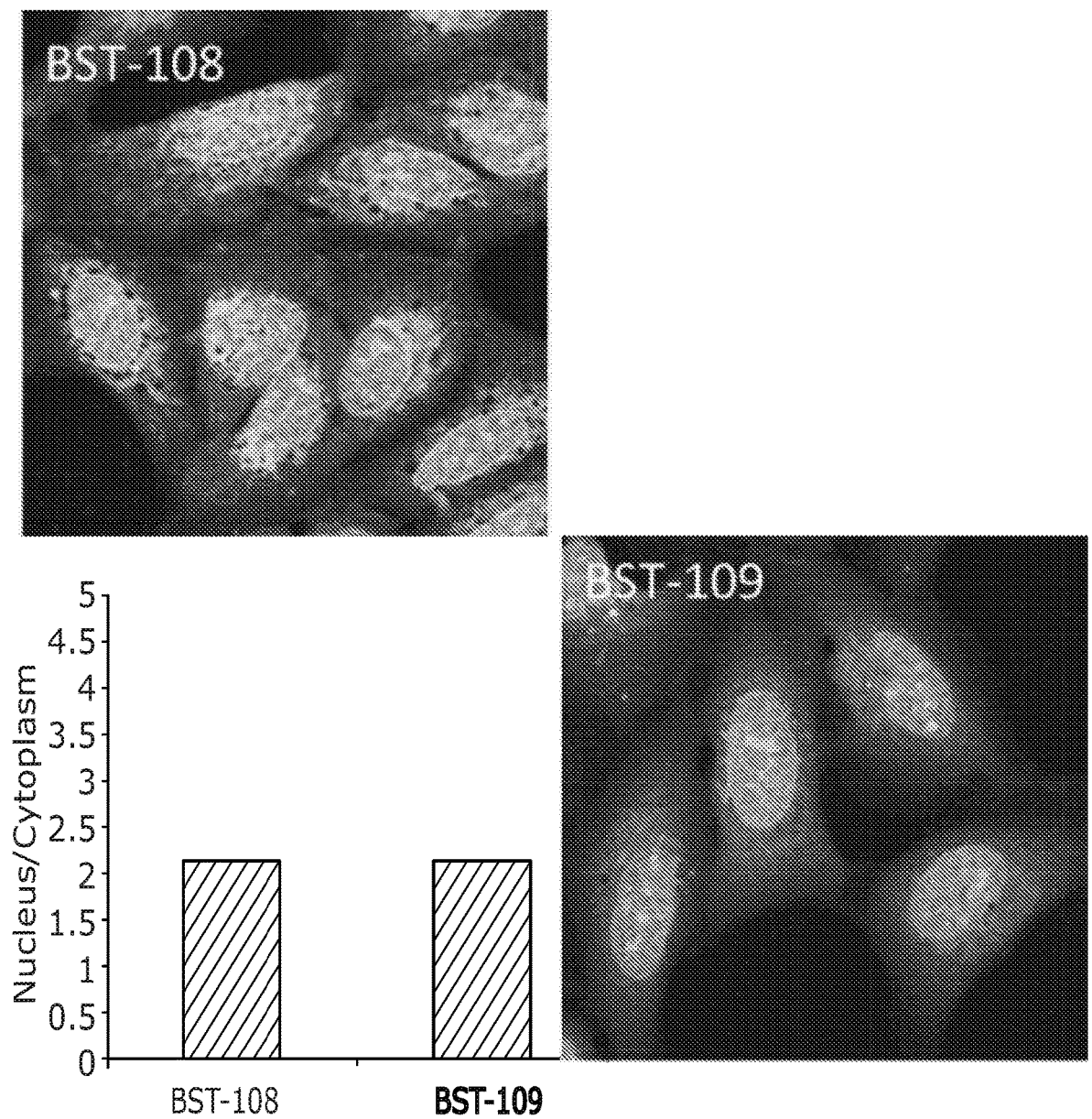
FIG. 5 shows fluorescence analysis via direct confocal imaging of compounds BST-108, BST-109.

The compounds BST-108, BST-109 were analysed in the same way. The results are shown in FIG. 5.

Analysis of BST-108, BST-109, BST-110 and BST-111 showed a strong nuclear uptake and perinuclear staining, with possible ER accumulation. A whole cell staining was a specific feature of BST-110 and BST-109, whereas BST-111 was mainly loaded in the nuclear compartment.

D. Consequences of AAQ Retention and Long Term Effects on Cell Viability

Timelapse imaging, in accordance with Errington R J et al, Time-lapse microscopy approaches to track cell cycle and lineage progression at the single-cell level, Curr Protoc Cytom. 2013 April; Chapter 12: Unit 12.4, was carried out in relation to cells with exposure to probe compounds.

In this regard, A549 cells were seeded in a 24 well coverslip bottomed-plate, cultured overnight in McCoys media for 24 or 48 hours. The plates were placed onto an inverted automated microscope, with the capacity for acquiring an image sequence of different wells (therefore exposure to different agent labelling). An Axiovert 100 microscope (Carl Zeiss, Welwyn Garden City, UK) was fitted with an incubator for 37° C./5% CO2 maintenance (Solent Scientific, Portsmouth, UK), and an ORCA-ER CCD camera (Hamamatsu, Reading, UK). Illumination was controlled by a shutter in front of the transmission lamp, and an x, y positioning stage with separate z-focus (Prior Scientific, Cambridge, UK) controlled multi-field acquisition. Image capture was controlled using Metamorph software.

Cells were exposed to a constant dose (0-5 µM) or a pulsed dose of 0 or 20 µM agent for 15 minutes followed by washout with warmed full media.

All images were collected with a ×10 (PH1) apochromat objective lens providing a field size of 500 times 500 microns. In this case a phase contrast image was collected every 30 minutes for 72 hours. Single cell growth and expansion can be tracked over time. The cells were harvested and run through a flow cytometry (typically a FACS Calibur 635 nm excitation/661/16 emission).

a) Constant Exposure to Probes

A549 cell lines were monitored using time-lapse collection and lineage progression, in constant exposure to compounds of the invention. The effects on cells were also determined.

In this regard, A549 cells were treated with probe compounds BST-101, BST-109, BST-110 and put on the time-lapse. Non-fluorescent images were collected over time. 72 hours later the cells were harvested and assayed using conventional flow cytometry and conventional methods for fluorescence intensity measurements to obtain relative fluorescence intensity (for example in units of channel number) and electronic gating (for example to determine the relative frequency of events) understood by those practised in the art, for (a) total signal of probe per cell determined by relative fluorescence intensity (arb. Units) and (b) cell cycle distribution across the cell compartments G1, S and G2 based on relative DNA content determined fluorometrically, and (c) cell viability determined by % total cells showing vital dye exclusion.

Figure 6:
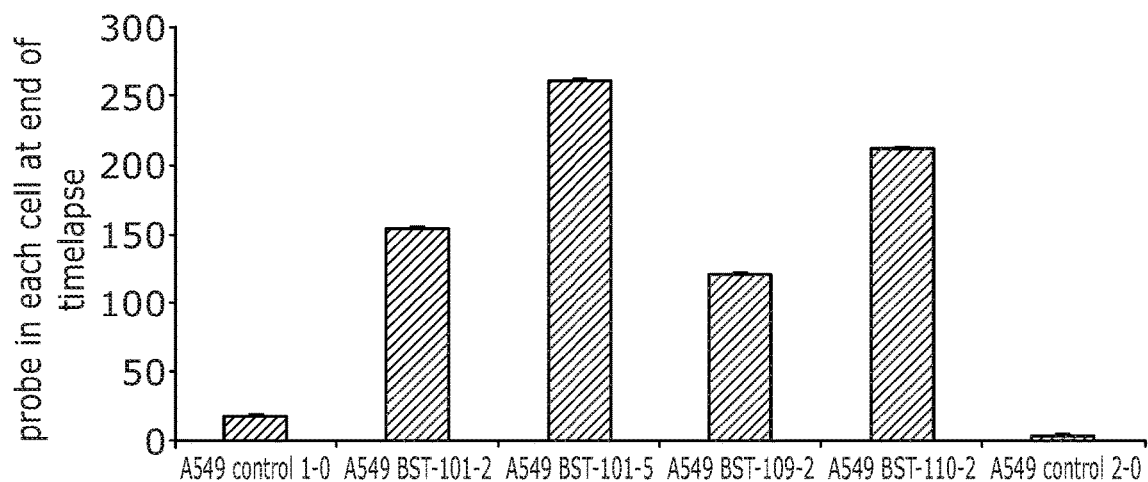
FIG. 6 shows analysis of A549 cells treated with compounds BST-101, BST-109, BST-110 after 72 hours, in terms of (a) total signal of probe per cell, (b) cell cycle distribution across the cell compartments G1, S and G2, and (c) cell viability.
Figure 6:
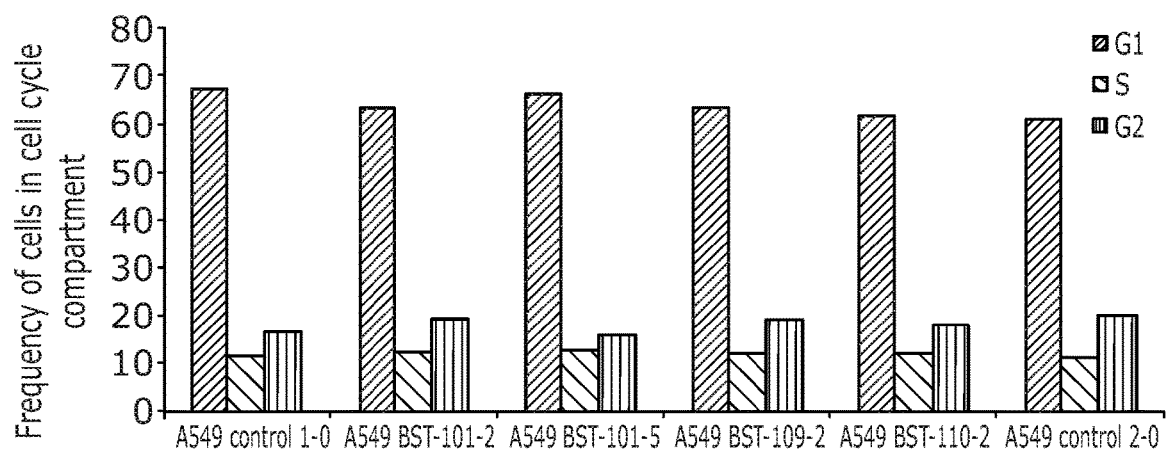
Figure 6:
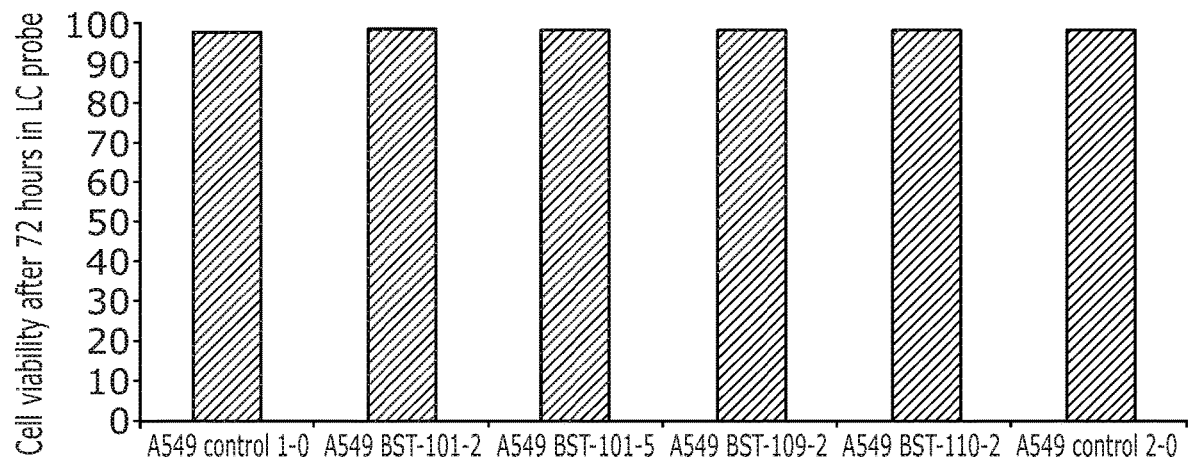

The results are shown in FIG. 6.

Analysis showed good viability with constant exposure and probe the capacity of maintaining cell labelling as well as cell expansion. All doses seemed to be non-perturbing to the cell cycle.

Within 24 hours the BST-109 and BST-110 are predominantly in a membrane compartment of the cytoplasm. The nucleus is now a low signal—the nuclear/cytoplasmic ratio is reversed.

b) Pulse Exposure to Probes

A549 cells were loaded with 20 uM BST-101, BST-109 or BST-110 for 15 mins followed by washout. Cells were then time-lapsed and reimaged after T=72 h, as before, Analysis showed BST-101 in A549 cells dividing, and signal retained in the same membrane compartment as at the start. BST-109 in A549 cells showed dividing, and signal retained but now relocated in a non-nuclear compartment perinuclear. BST-110 in A549 cells gave dividing, and signal now relocated in a non-nuclear compartment perinuclear.

c) Cellular Viability (Proliferation)

The viability of A549 or MCF7 in response to compounds was determined using the MTT (3-(4,5-dimethylthiazolyl-2-)-2, 5-diphenyltetrazolium bromide) assay according to the protocol set out in Mosmann T., Rapid colorimetric assay for cellular growth and survival: application to proliferation and cytotoxicity assays. Journal of immunological methods 1983; 65:55-63.

Initially, cells were seeded into a rounded-bottom 96 well plate (Corning) at six different cell seeding densities (0.5× 104, 1×104, 2×104, 3×104, 4×104, and 5×104) per mL of R10 media (cells/mL) in order to optimise the assay and establish the most suitable seeding assay. Concentration of 1×104 cells/mL was determined to be the optimum seeding density for both cell lines for 96 h total incubation. A control lane contained supplemented R10 only. The 96 well plates were incubated overnight at 37° C., 5% CO2 and 100% humidity to allow cell adhesion. Cells were then treated respectively with novel AAQs (0.25-100 µM) or growth inhibition ($IC_{50}$) of compounds of the invention was studied against MCF7 and A549 cancer cell lines. Compounds were tested with a concentration range between 0.25 and 100 µM for 72 h and doxorubicin, as positive cytotoxic control, was tested in parallel at the same doses.

The $IC_{50}$ values are shown in Tables 3 and 4.

TABLE 3

| Compound | MCF7 (µM) | $R^2$ value | A549 (µM) | $R^2$ value |
|---|---|---|---|---|
| Doxorubicin | 0.028 | 0.1831 | 0.05 | 0.1759 |
| BST-101 | 0.750 | 0.7865 | >100 | 0.9034 |
| BST-102 | 1.75 | 0.6174 | >100 | 0.2725 |
| BST-106 | 11.3 | 0.5697 | 11.7 | 0.568 |
| BST-107 | 1.66 | 0.5541 | 17.5 | 0.9475 |
| BST-108 | 1.44 | 0.4437 | 1.7 | 0.7563 |
| BST-109 | 15.70 | 0.7976 | 22.5 | 0.7371 |
| BST-110 | 19.5 | 0.7258 | 22.3 | 0.9473 |
| BST-111 | 1.8 | 0.757 | 38.2 | 0.9546 |

TABLE 4

| Compound | MCF-7 (µM) | $R^2$ value | A549 (µM) | $R^2$ value |
|---|---|---|---|---|
| BST-101 hydrolysed | 56.73* | 0.9434 | >100 | 0.9621 |
| BST-102 hydrolysed | <0.250* | 0.8793 | >100* | 0.8352 |
| BST-106 hydrolysed | 40* | 0.933 | >100* | 0.8502 |
| BST-107 hydrolysed | 29.51 | 0.7825 | 12.7 | 0.7826 |
| BST-108 hydrolysed | <0.250 | 0.3528 | 1.24 | 0.6786 |
| BST-109 hydrolysed | 2.26 | 0.5933 | 34 | 0.8435 |
| BST-110 hydrolysed | 20.11 | 0.723 | 45.2 | 0.8345 |
| BST-111 hydrolysed | 8.60 | 0.6085 | 32.3 | 0.6153 |

*Solubility problems, blue crystals appeared after 48 h of treatment. R2 is a statistical measure of how well the regression line approximates the real data points.

Further tests were carried out against A2780, 2780AD and MCP1 cell lines. The results are shown in Table 5.

TABLE 5

| Compound | | n | A2780 | 2780/cp70 | RF | MCP1 | RF | 2780AD | RF |
|---|---|---|---|---|---|---|---|---|---|
| BST-302 | A | 1 | 1.89 ± 0.40 | 0.60 ± 0.03 | 0.32 | 1.16 ± 0.36 | 0.61 | 153.9 ± 28.9 | 81.4 |
| BST-303 | A | 2 | 58.6 ± 6.6 | 10.9 ± 2.0 | 0.19 | 21.1 ± 3.8 | 0.36 | 570.3 ± 122.1 | 9.7 |
| BST-304 | A | 3 | 82.1 ± 12.7 | 5.8 ± 1.5 | 0.07 | 29.6 ± 5.6 | 0.36 | 996.3 ± 15.0 | 11.8 |
| BST-305 | A | 4 | 284..3 ± 33.7 | 39.8 ± 4.5 | 0.14 | 150.7 ± 7.2 | 0.53 | 1489.7 ± 90.9 | 5.2 |
| BST-301 | A | 5 | 695.5 ± 109.2 | 72.2 ± 5.8 | 0.10 | 268.7 ± 54.8 | 0.39 | 1912.3 ± 229.2 | 2.8 |
| BST-200 | B | 1 | 964.0 ± 23.0 | 88.0 ± 14.0 | 0.09 | 253.0 ± 5.0 | 0.26 | 2758.0 ± 116.0 | 2.9 |
| BST-300 | B | 5 | 7.10 ± 0.36 | 1.18 ± 0.14 | 0.17 | 2.60 ± 0.43 | 0.37 | 7.59 ± 0.83 | 1.07 |
| Cisplatin | — | — | 0.38 ± 0.04 | 2.04 ± 0.10 | 5.37 | 0.48 ± 0.08 | 1.26 | 1.73 ± 0.13 | 4.6 |

Flow Cytometry

Flow cytometry analysis was performed to evaluate the effect of pre-treatment with HCl to generate an active aldehyde on the cell uptake properties. A549 cells were incubated for 30 min with compounds of Formula (I) and its hydrolysed forms (20 µM) prior to analysis. The rate of uptake was tested in A549 cell culture media and in Aldefluor buffer, containing the MDR-blocker verapamil (Pearce and Bonnet 2007), to evaluate the effect in uptake with/without the Aldefluor assay system. Analysis was conducted in the viable subset of cells, corresponding to ~95% of the total amount under investigation.

Figure 7:
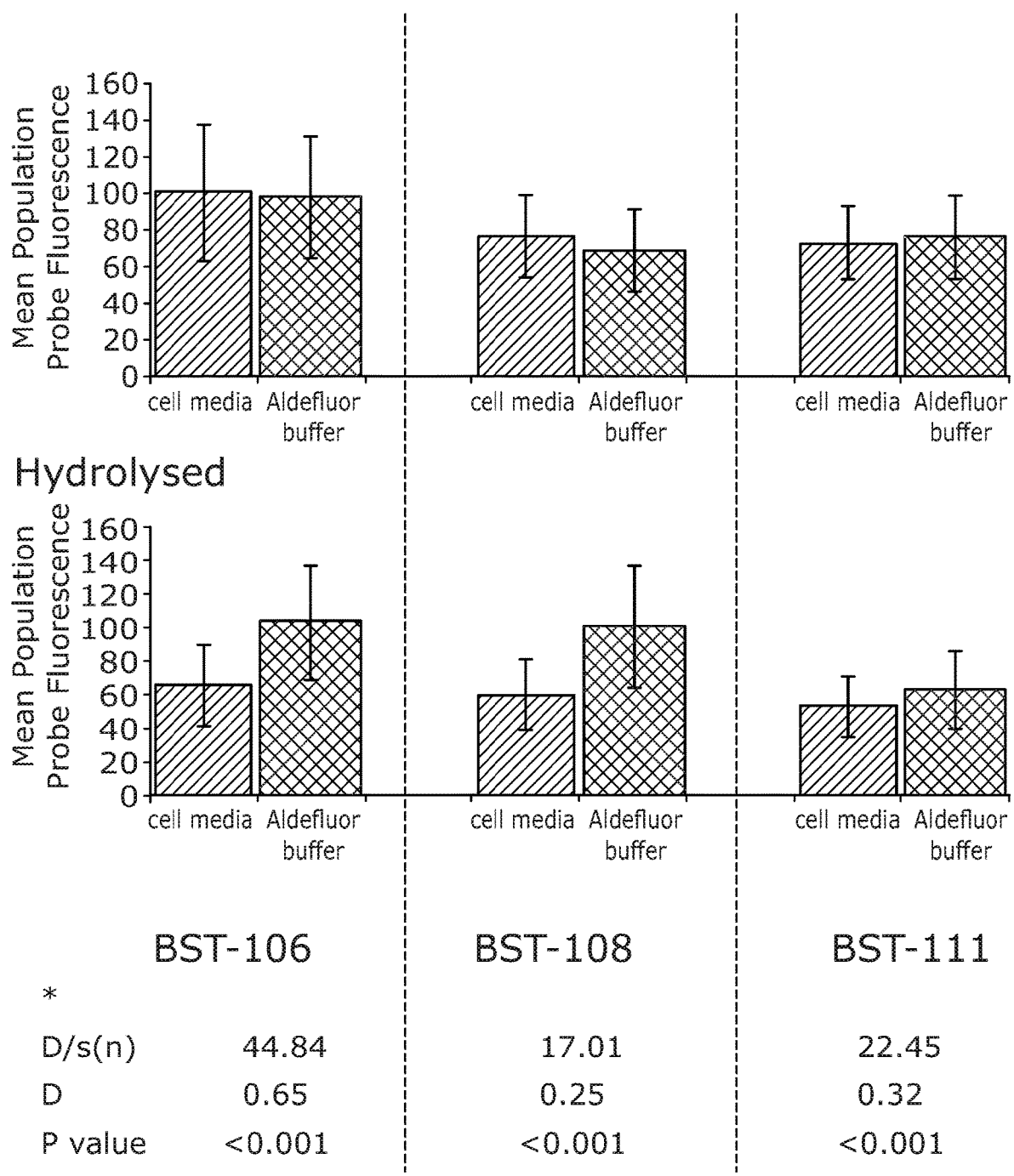
FIG. 7 shows K-S statistical analysis of compounds BST-106, BST-108, BST-111, and hydrolysed forms thereof, uptake in Aldefluors buffer.

FIG. 7 shows the uptake profiles of BST-106, BST-108, BST-111 compounds and their hydrolysed forms (generated after exposure to 2M HCl for 30 min) in A549 cell line versus Aldefluor buffer. Aldefluor buffer contained verapamil vs. cell media. The cells were incubated with 20 µM of the respective AAQ/HAAQs (30 min) before analysis Statistical analysis of A549 uptake before/after hydrolysis was also studied. Experiments were performed in cell media versus Aldefluor buffer. Data were processed using FlowJo software (Tree Star). DRAQ5 was used to set the dynamic range and as control dye and empty cells were used to determine auto-fluorescence.

TABLE 6

| A549 sample | Solution | Median | Covariance | SD | % ile (25) |
|---|---|---|---|---|---|
| Empty | media | 15.94 | 31.29 | 31.29 | 13.48 |
| DRAQ5 | media | 217.4 | 31.61 | 31.61 | 191.27 |
| BST-106 | media | 101.48 | 34.58 | 34.58 | 84.64 |
| | buffer | 96.13 | 32.87 | 32.87 | 81.66 |
| BST-106 hydrolysed | media | 64.9 | 35.28 | 35.28 | 55.56 |
| | buffer | 102.97 | 31.38 | 31.38 | 86.76 |
| B | media | 75.48 | 28.15 | 28.15 | 65.32 |
| | buffer | 67.08 | 32.09 | 32.09 | 57.65 |
| BST-108 | media | 51.51 | 33.5 | 33.5 | 44.66 |
| hydrolysed | buffer | 61.44 | 38.88 | 38.88 | 51.25 |
| BST-111 | media | 72.42 | 26.78 | 26.78 | 62.72 |
| | buffer | 74.94 | 28.85 | 28.85 | 64.64 |
| BST-111 | media | 59.33 | 32.6 | 32.6 | 49.93 |
| hydrolysed | buffer | 57.89 | 35.36 | 35.36 | 48.48 |

* Low loader cell population (representative of SP)

SUMMARY OF FINDINGS

Spectral and Fluorescence Properties

Although anthraquinones typically have very low quantum yields (as described in Njoh K L et al, Spectral analysis of the DNA targeting bisalkylaminoanthraquinone DRAQ5 in intact living cells, Cytometry A 2006; 69:805-14) this can make them ideal probes for performance as a contrast agent for both fluorescence detection due to cell accumulation and for photoacoustic imaging. Accordingly, low quantum yield molecules such as those described in the present invention, including their hydrolysed and deuterated forms, that also have differential cellular uptake, subcellular localization and persistence profiles can co-display advantageous photoacoustic for use in cell-based assays. AQ-derived molecules can also provide advantageous properties for detection by SERS in cell-based assays.

Absorption spectroscopy and fluorescence spectroscopy was used to show that the compounds of the present invention have far red to near-IR fluorescence properties. Near infrared (NIR) emissive compounds have advantages in the development of fluorescent probes and labelling for bio-imaging in living systems since fluorescence in the long-wavelength region would generate minimum photo-toxicity to biological components, deep tissue penetration and minimal background from auto-fluorescence by bio-molecules.

Therefore, compounds of the invention are useful for analysing biological samples comprising cells, which may be dead, fixed or living or other biological material containing nucleic acid.

Binding Properties

The compounds of the present invention showed intrinsic ability to bind to nucleic acids.

Therefore, compounds of the invention may be used in nuclear discrimination assays.

Labelling Properties of Fixed and Live Cells

The compounds of the invention can be used as nuclear counterstains.

Fixed cell-based and live cell-based imaging assays were used to evaluate cell labelling. Fluorescence of compounds in two fixed and live cell models, U-2 OS and A549 was determined to evaluate their ability to fluorescently label cells with or without the involvement of membrane limiting or active uptake systems.

These analyses showed localization in live cells. Some compounds displayed a nuclear signal greater than membrane signal and therefore they may be use as a live cell labelling ratiometric probes for cell identification. Other compounds showed preferential membrane (Golgi and/or ER) locations and exclusion from nucleus and therefore they may be use as a live cell labelling probes with negative nuclear labelling.

Nuclear counterstains are important tools for many fluorescence-based cell analyses, including but not limited to microscopy, flow cytometry and in-cell western analysis.

The compounds of the invention provide stable fluorophores with structure-dependent subcellular localization and a lack of toxic effects consistent with differential accumulation in endoplasmic reticulum, Golgi or nucleus.

Therefore, labelling experiments showed that compounds of the invention have differential distribution within the cytoplasmic and nuclear compartments thereby providing for pattern based recognition and image-masking methods stained cell nuclei.

The use of the compounds of the present invention as a discriminating or orientating parameter for cell nuclei has been demonstrated for both flow cytometry and confocal laser scanning microscopy.

The invention claimed is:

1. A compound of any one of Formulae (I), (Ib), (Id), (II), (III) or (IV), as defined below:

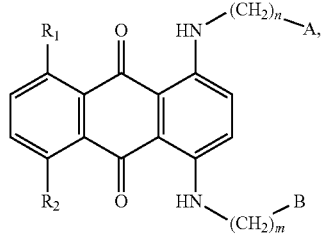
(I)

wherein n and m are independently selected from 1, 2, 3, 4, 5, and 6,

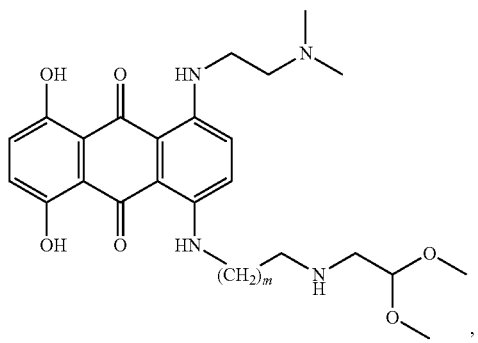
(Ib)

wherein m is 1, 2, 3, 4 or 5,

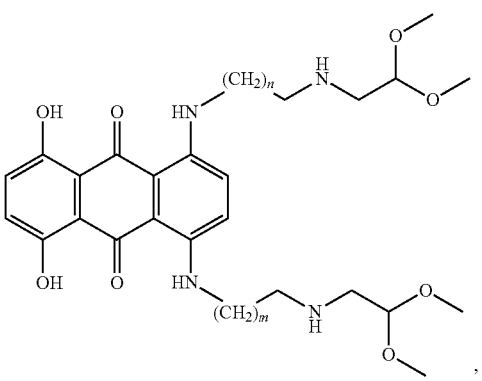
(Id)

wherein n and m are the same and selected from 1, 2, 3, 4, 5, and 6,

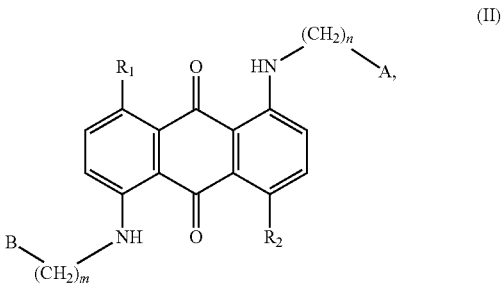
(II)

wherein n and m are independently selected from 1, 2, 3, 4, 5, and 6,

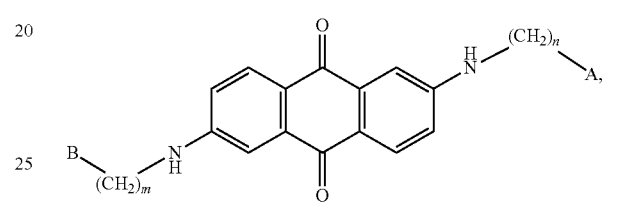
(III)

wherein n and m are independently selected from 1, 2, 3, 4, 5, and 6,

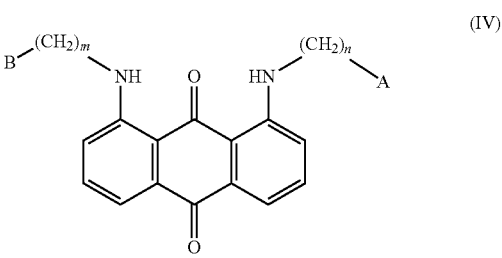
(IV)

wherein
$R_1$ and $R_2$, when present, are each independently selected from —OH or H, or $CH_3$, halo or OR, wherein R is selected from —$CH_3$, —$CH_2OCH_3$, —$CH(CH_3)_2$, —$COCH_3$, —$CH_2CH$=$CH_2$, benzene and benzyl;
and either:
(i) A and B are each independently of formula: —$R^aCH_2CH(OR^b)_2$;
or
(ii) one of A and B is of formula: —$R^aCH_2CH(OR^b)_2$ and the other one is of formula: —$NR^b_2$;
wherein
the or each $R^a$ is independently selected from —$CH_2$—, —C(=O)NH—, —NHC(=O)—, —C(=O)—, —C(=$CH_2$)—, —C(=$CHCH_3$)—, —N($CH_3$)—, and —N(alkylaryl)- and each $R^b$ is independently selected from —$CH_3$, —$CH_2CH_3$, —$CH(CH_3)_2$, and —$CH_2CH$=$CH_2$.

2. The compound of claim 1, wherein $R_1$ and $R_2$ are the same.

3. The compound of claim 2, wherein $R_1$ and $R_2$ are both H.

4. The compound of claim 2, wherein $R_1$ and $R_2$ are both OH.

5. The compound of claim 1, wherein the or each $R^a$ is independently selected from —$CH_2$—, —$C(=O)NH$—, —$NHC(=O)$—, —$C(=O)$—, —$C(=CH_2)$—, and —$C(=CHCH_3)$—.

6. The compound of claim 5, wherein the or each $R^a$ is independently selected from
—$CH_2$—, —$C(=O)NH$—, and —$NHC(=O)$—.

7. The compound of claim 1, wherein the or each $R^b$ is independently selected from
—$CH_3$, —$CH_2CH_3$, and —$CH_2CH=CH_2$.

8. The compound of claim 7, wherein the or each $R^b$ is —$CH_3$.

9. The compound of claim 1, wherein A and B are each independently of formula:
$R^aCH_2CH(OR^b)_2$; and m and n are the same.

10. The compound of claim 9, wherein m and n are 1 or 2.

11. The compound of claim 1, wherein A and B are each independently of formula:
$R^aCH_2CH(OR^b)_2$; and A and B have the same $R^a$ group.

12. The compound of claim 11, wherein each $R^a$ is selected from —$CH_2$—, —$C(=O)NH$—, and —$NHC(=O)$—.

13. The compound of claim 1, wherein A and B are each independently of formula:
—$R^aCH_2CH(OR^b)_2$; and A and B have the same $R^b$ group.

14. The compound of claim 13, wherein each $R^b$ is —$CH_3$.

15. The compound of claim 1, wherein A and B have the formula: —$R^aCH_2CH(OR^b)_2$; and A and B are the same.

16. The compound of claim 1, wherein A is of formula: —$NR^b_2$ and B is of formula —$R^aCH_2CH(OR^b)_2$, m is 1 or 2 or 3 or 4 or 5 and n is 1 or 2 or 3.

17. The compound of claim 16, wherein m is 1 or 2 or 3 or 4 or 5 and n is 2.

18. The compound of claim 1, wherein one of A and B is of formula: —$R^aCH_2CH(OR^b)_2$ and the other one is of formula: —$NR^b_2$; and A and B have the same $R^b$ group.

19. The compound of claim 18, wherein $R^b$ is $CH_3$.

20. A fluorescent complex comprising a nucleic acid and a compound as defined in claim 1.

21. A method of analysing a biological sample comprising cells, or other biological material containing nucleic acid, the method comprising the steps of:
a) preparing a biologically compatible solution containing a compound as defined in claim 1;
b) treating a biological sample with the biologically compatible solution; and
c) detecting a spectroscopic property associated with the absorption of electromagnetic radiation by the compound.

22. The method of claim 21 wherein the spectroscopic property associated with absorption of electromagnetic radiation by the compound is:
(i) fluorescence, or
(ii) a colorimetric property, or
(iii) a photoacoustic property, or
(iv) a Raman scattering property.

23. A method of staining a biological sample comprising cells or other biological material containing nucleic acid, which method comprises contacting the biological sample with a compound as defined in claim 1.

24. The method of claim 23, wherein the method comprises contacting the biological sample with the compound and then:
carrying out a fluorescence-based detection step; or
carrying out a Raman scattering-based detection step; or
carrying out a photoacoustic-based detection step.

25. The method of claim 23, which comprises the steps of:
a) preparing a biologically compatible solution containing the compound for contacting the biological sample;
b) treating a biological sample with the biologically compatible solution for a time sufficient to cause staining;
c) illuminating the stained sample with a light source sufficient to excite the compound; and
d) detecting the emitted fluorescence from the sample using a fluorescence detection instrument.

26. A method of quantifying nucleic acid content in live cells, comprising:
combining a compound as defined in claim 1 with a sample to form a mixture, wherein the sample comprises a nucleic acid molecule;
incubating the mixture for a sufficient amount of time for the compound to associate with the nucleic acid in the sample;
illuminating the incubated sample with an appropriate wavelength to generate a detectable optical response or photoacoustic response; and
detecting the presence of nucleic acid in the sample by flow cytometric analysis, image cytometry analysis, image analysis including, or high content image analysis.

27. A kit for carrying out an assay, which includes a compound as defined in claim 1, and further including one or more of the following: buffering agents, sample preparation reagents, additional detection reagents, organic solvent, other fluorescent detection probes, standards, microspheres, specific cell lines, antibodies and/or instructions for carrying out an assay.

\* \* \* \* \*